US009353453B2

(12) United States Patent
Chiesa et al.

(10) Patent No.: US 9,353,453 B2
(45) Date of Patent: May 31, 2016

(54) METAL SUBSTRATE MODIFIED WITH SILICON BASED BIOMIMETIC TREATMENT HAVING ANTIBACTERIAL PROPERTY FOR THE OSTEOINTEGRATION THEREOF

(75) Inventors: Roberto Chiesa, Milan (IT); Alberto Cigada, Milan (IT); Cinzia Della Valle, Milan (IT)

(73) Assignee: POLITECNICO DI MILANO, Milan (IT)

( * ) Notice: Subject to any disclaimer, the term of this patent is extended or adjusted under 35 U.S.C. 154(b) by 820 days.

(21) Appl. No.: 13/553,240

(22) Filed: Jul. 19, 2012

(65) Prior Publication Data
US 2014/0021055 A1 Jan. 23, 2014

(51) Int. Cl.
C25D 11/02 (2006.01)
C25D 11/26 (2006.01)

(52) U.S. Cl.
CPC .............. *C25D 11/026* (2013.01); *C25D 11/26* (2013.01)

(58) Field of Classification Search
CPC ............................. C25D 11/026; C25D 11/26
USPC .................................................. 205/318, 322
See application file for complete search history.

(56) References Cited

U.S. PATENT DOCUMENTS

| 5,152,993 A | 10/1992 | Bjursten et al. |
| 5,385,662 A | 1/1995 | Kurze et al. |
| 5,478,237 A | 12/1995 | Ishizawa |
| 5,885,612 A | 3/1999 | Meconi et al. |
| 2010/0316686 A1* | 12/2010 | Dingeldein et al. .......... 424/422 |

FOREIGN PATENT DOCUMENTS

| CN | 1018662269 | 10/2010 |
| EP | 1515759 | 3/2005 |
| EP | 2037594 | 3/2009 |
| WO | WO 2010013120 A1 * | 2/2010 |

OTHER PUBLICATIONS

"Development and Characterization of Antibacterial Treatments for Titanium Obtained by Anodic Spark Deposition" by Simone Panzuto, Thesis published Jul. 20, 2011 accessed from http://hdl.handle.net/10589/21037.*
Lv et al., "Effects of Current Frequency on the Structural Characteristics and Corrosion Property of Ceramic Coatings Formed on Magnesium Alloy by PEO Technology" J. Mater. Process. Technol. 208, pp. 9-13 (2008).*

* cited by examiner

*Primary Examiner* — Bryan D. Ripa
(74) *Attorney, Agent, or Firm* — Silvia Salvadori, P.C.; Silvia Salvadori

(57) ABSTRACT

A substrate of a metal selected from the group consisting of titanium, tantalum, titanium alloys and tantalum alloys, modified by anodic spark deposition (ASD) on the surface thereof of a microporous and nanoroughened layer of the oxide of the same metal, said layer being enriched with Ca, P, Si, Na, and at least one metal selected from Ag and Ga.
This surface modified metal substrate show excellent osteointegrating properties associated with antibacterial activity. A further advantage resides in that its preparation process does no longer require alkaline etching to promote cellular adhesion.

15 Claims, 24 Drawing Sheets

Figure 6
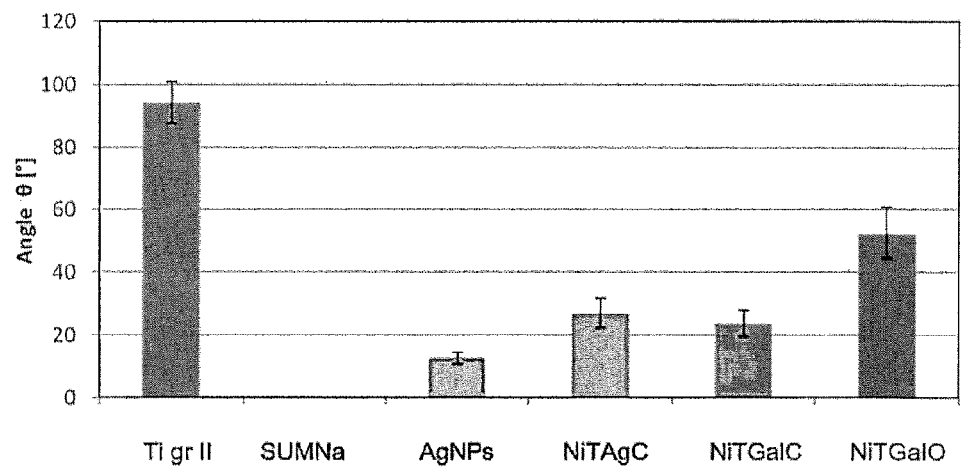
Figure 7A                Figure 7B
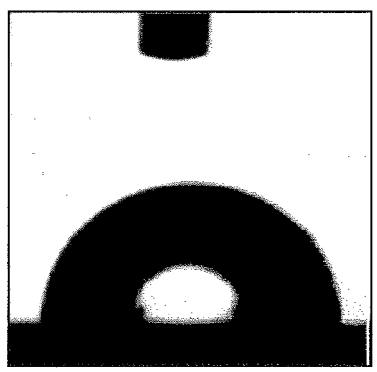 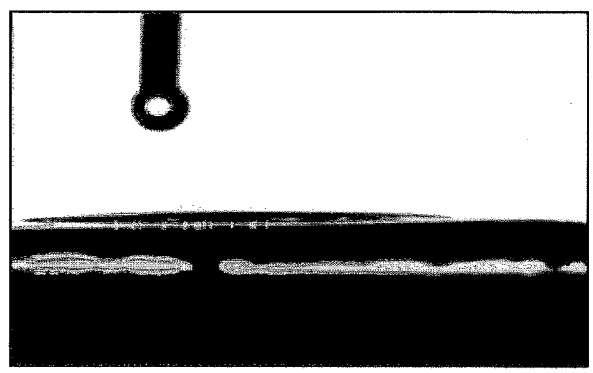

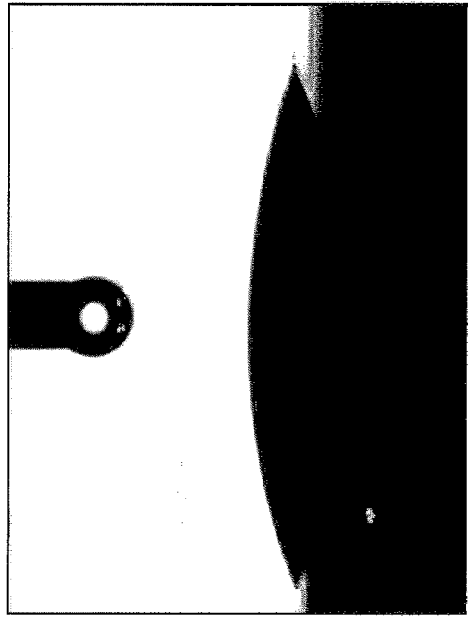
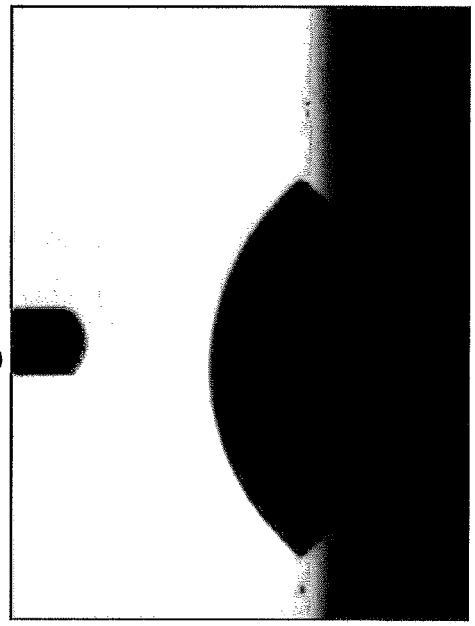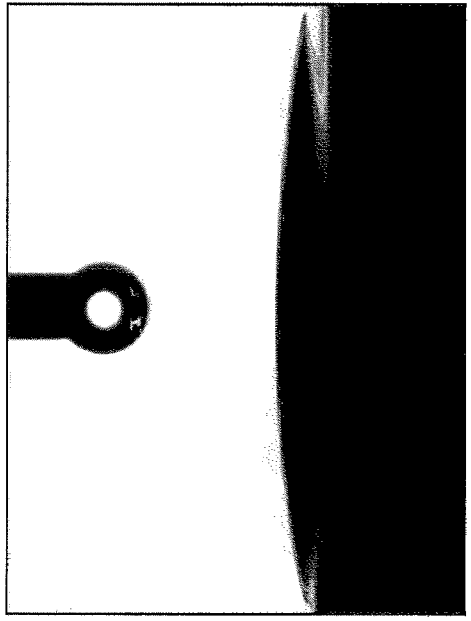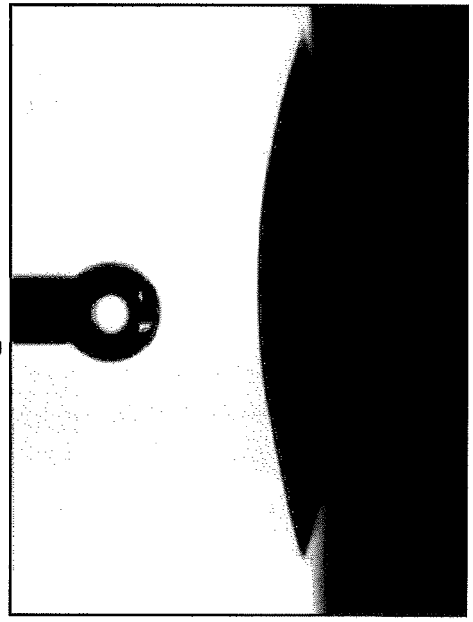

METAL SUBSTRATE MODIFIED WITH SILICON BASED BIOMIMETIC TREATMENT HAVING ANTIBACTERIAL PROPERTY FOR THE OSTEOINTEGRATION THEREOF

TECHNICAL FIELD

The present invention relates to a substrate of a metal selected from the group consisting of titanium tantalum, titanium alloys and tantalum alloys, modified by anodic spark deposition on the surface thereof with silicon based coating, characterized by having antibacterial properties, the process for preparing this surface modified substrate and surgical implants comprising and more preferably consisting of this metal substrate.

BACKGROUND OF THE INVENTION

In the field of prosthodontics, orthopedic joint prosthetics and dental implantology it has been found that the compatibility of the materials used for prostheses with biological tissues is fundamentally important to allow adequate treatment of the patients.

The materials commonly used in these fields consist substantially of metallic substrates of steel titanium or tantalum, which have excellent mechanical properties but require long times for integration in the biological tissues of the patients, in which they are implanted and for healing of the implantation region.

In order to overcome these drawbacks, methods have been developed which are suitable to modify the surface topography and chemistry of the metallic substrates by introducing thereon chemical groups or chemical elements capable of interacting with biological tissues and thus allowing integration between the prosthesis and the tissues. These methods are able to modify the surfaces reproducing the chemical composition and/or the topographical aspect of the tissue in which the material will be in contact in the biological environment. These methods are generally known as biomimetic treatments. For example U.S. Pat. No. 5,385,662 describes the modification of metallic surfaces by means of a hydrogen peroxide treatment in order to deposit a layer of metallic oxides on said surfaces. This method, however, is not described for use in the biomedical field. U.S. Pat. Nos. 5,152, 993 and 5,885,612 describe a treatment of metallic surfaces by using hydrogen peroxide and optionally metallic ions in order to modify the surfaces of metallic prostheses by introducing hydroxyl (—OH) groups thereon.

EP068300, on the other hand, describes the treatment of metallic surfaces by immersion in alkaline solution of NaOH, followed by washing and high temperature thermal treatment. This method, too, introduces —OH groups, which are suitable for interaction with bone tissues, on the treated metallic surface.

Moreover U.S. Pat. No. 5,478,237 describes the use of anodic deposition on the surface of bone implants with the object of modifying the composition and morphology of the metallic substrate. Although the introduction of —OH groups is not described, the process of U.S. Pat. No. 5,478,237 leads to the formation of a porous layer rich in calcium and phosphorous on the surface of implants facilitating the osteointegration thereof.

EP 1,515,759 in the name of the Applicant teaches the use of a double step of anodic deposition to deposit on the surface of the metallic implant a microporous layer of calcium and phosphorus, and at the same time introducing —OH groups.

An improvement to the technology disclosed in the above patents is disclosed in EP2307594 as it allows to introduce on the surface of the metallic substrate by ASD deposition of chemical elements, such as Ca, P, Si, and Na that are suitable to increase the biomimetic properties of the surface modified metallic substrate and also provide —OH groups with a successive treatment with an NaOH solution of the substrate coming from ASD deposition, without resorting to multiple anodic layers deposition as described in the aforementioned method of EP1,515,759.

Although the technology described in EP2307564 represents a considerable improvement if compared to the prior art of metallic substrates used for osteointegrative purposes, it does not solve the problem connected with the insurgence of bacterial infections.

Clinical practice reports that bacterial infections occurring in implanted devices represents one of the commonest causes of failure of these implanted devices: with the consequent removal of the same implant from the host organism and replacement thereof bring to an increase of health care costs as well as social costs, also taking into account that the antibiotic and pharmacologic treatment results in most cases ineffective in this field.

CN101862269 abstract describes an implant in titanium enriched with only calcium and phosphorus having on the surface grains of Ag in the form of nanoparticles which is provided with antibacterial activity, however it is not clear from the abstract the technique used to obtain this implant.

To date metallic substrates obtained by ASD technique possessing both a high osteointegrative activity and contemporaneously showing antibacterial properties are not available, since the surface treatments of metallic substrate are directed to limit the adhesion or proliferation of bacteria, but they result not possessing any osteointegrative activity as in most cases they resulted toxic for the eukaryotic cells of the host's tissue.

Therefore an object of the invention is to modify the morphology of the metallic substrates, giving them a structure that is suitable for interacting in an optimal level with biological tissues and contemporaneously shows antibacterial properties.

Another object of the invention is to provide a biomimetic treatment of metallic substrates, that is highly reliable, relatively easy to be provided and at competitive costs.

Therefore a further subject of the present invention relates to a prosthesis or a component thereof or an implant comprising or completely made of this material.

SUMMARY OF THE INVENTION

These and other object of the invention are fulfilled by the surface modified metals substrates as claimed in the appended claims.

In particular the present invention relates to substrate of a metal selected from the group consisting of titanium, tantalum, titanium alloys and tantalum alloys, modified by anodic spark deposition on the surface thereof with a microporous and microroughened layer of the oxide of the same metal enriched with Ca, P, Si, Na, and at least one metal selected from Ag and Ga.

The present invention further relates to a process for preparing the substrate according to the present invention, comprising the essential step of subjecting the metal substrate to an anodic spark deposition (ASD) treatment in an aqueous solution comprising sodium silicate hydrate ($Na_2SiO_3 \cdot 2H_2O$), β-glycerophosphate (β-GP), calcium acetate hydrate ($C_4H_6CaO_4 \cdot H_2O$), sodium hydroxide (NaOH), at least one of the following components: elemental Ag nanoparticles, an Ag or Ga salt.

The metallic substrate of the invention obtained with the above process allows to achieve the following targets.

The oxide film present on the surface of the metallic substrate is characterized by having excellent osteointegrative activity associated with antibacterial properties.

These excellent osteointegrative properties are moreover obtained with the above sole step of ASD deposition and surprisingly with the process of the invention it is no longer necessary the subsequent thermal treatment with NaOH concentrated solution for providing OH groups essential in the process described in EP2037594.

The above moreover representing a considerable improvement in the economy of process.

DESCRIPTION OF THE FIGURES

FIG. 6: Surface wettability as a function of the static contact angle, of the samples undergoing ASD treatment with respectively AgNPs, NITAgC, NITGalC, NITGalO and SUMNa (control)

FIGS. 7A and 7B: photos of water drop morphology on the following samples: A) Titanium Grade; and II B) sample obtained by ASD treatment with SUMNa (control).

FIGS. 8A-8D: photos of water morphology on samples undergoing ASD treatment with respectively: A) AgNPs, B) NITAgC, C) NITGalC and D) NITGalO.

DETAILED DESCRIPTION OF THE INVENTION

Figure 1A:
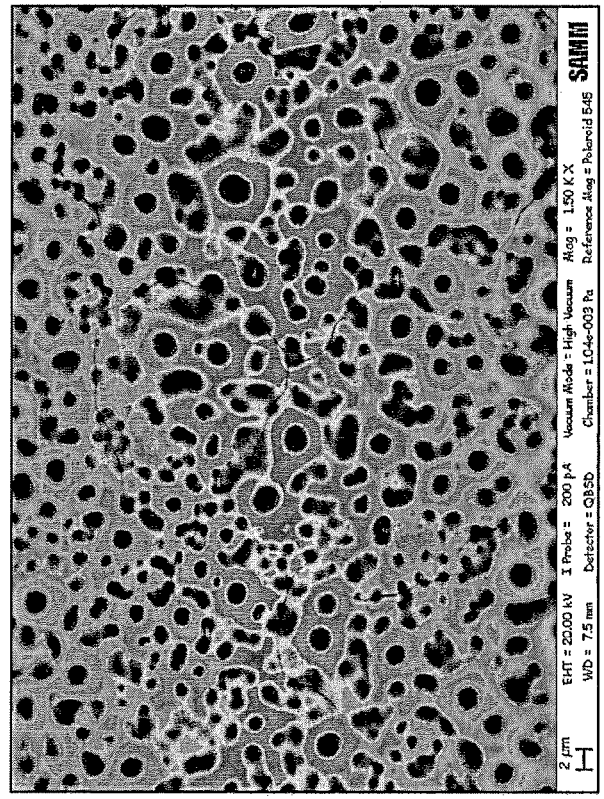
FIGS. 1A-1E: SEM Micrography 1500X magnification of samples undergoing ASD treatment with respectively: A) AgNPs, B) NITAgC, C) NITGalC, D) NITGalO, and E) SUMNa (Control).

In a preferred embodiment of the process of the invention, when the solution contains a salt it is preferably selected from silver nitrate ($AgNO_3$), silver acetate ($CH_3COOAg$), gallium nitrate $Ga(NO_3)_3$.

In a further more preferred embodiment the solution, besides the aforementioned salt it also contains a chelating agent in order to avoid possible precipitation of silver and gallium salt. This chelating agent is preferably selected from the group consisting of: L-cysteine ($HSCH_2CH(NH_2)CO_2H$), oxalic acid dihydrate ($HO_2CCO_2H*2H_2O$).

In the process for preparing the metallic substrate according to the present invention the deposition aqueous solution preferably comprises sodium silicate hydrate in concentrations of from 0.005 M to 0.1 M, β-glycerophosphate in concentrations of from 0.03 M to 0.2 M, calcium acetate hydrate in concentrations of from 0.05 M to 0.6 M, and NaOH in concentrations of from 0.005 M to 0.4 M, and from 1 to 10 g/l of elemental Ag and/or from 0.001 to 0.01 M of a silver and/or gallium salt.

When the aqueous solution contains also a chelating agent, the latter is present in concentrations from 0.001 to 0.5 M.

According to a particularly preferred embodiment of the process of the invention the deposition aqueous solution comprises 0.03 M sodium silicate hydrate, 0.1 M β-glycerophosphate, 0.3 M calcium acetate hydrate, 0.036M NaOH.

When elemental silver is present, it is preferably in the form of elemental Ag nanoparticles at concentration of 3 g/l with a particle size between 10 and 250 nm. When silver is in the form of a silver salt its concentration is preferably 0.004M and more preferably it also contains as chelating agent 0.002M L-cysteine.

When gallium nitrate is added to the aforementioned preferred aqueous solution, the concentration thereof in said aqueous solution is preferably 0.004 M and the same aqueous solution contains 0.006M L-cysteine.

In alternative gallium nitrate may be added at the same concentration 0.004M in the presence of 0.306M oxalic acid as chelating agent.

In a preferred embodiment the anodic spark deposition ASD is performed at a temperature comprised in an interval of 0±0.5° C.

In a further preferred embodiment ASD step is performed by working at a first current density value of from 5 to 50 more preferably 10 $mA/cm^2$, with a potential that increases freely up to a value of 210 to 330V, more preferably from 300 and 325 V, for a period of time needed to reach said potential value and a second current density value of from 50% to 5% more preferably 20% of said current density.

In a further embodiment the process according to the present invention may further encompass a step of cleaning the metal substrate before the anodic deposition ASD, by immersing the substrate in a ultrasound tray containing acetone for a first period of time of from 3 to 5 minutes and distilled water for a second period of time of from 3 to 5 minutes. In a further embodiment the process according to the present invention further comprises the step of further cleaning the metal substrate coming from ASD treatment with water by immersion of the same in distilled water and final drying.

The following examples of preparation of the metallic substrates of the invention and also the results of the experimental tests carried out on said metallic substrates compared with the metallic substrates of the prior art are herewith reported only for illustrative purposes.

EXAMPLE 1

Preparation of the Metallic Substrates Obtained with the Treatment AgNPs (Ag Nanoparticles)

This treatment consists in the following operating conditions:
1. Superficial cleaning of grade II titanium sample, using an ultrasound tray for 3-5 minutes in acetone and for 3-5 minutes in distilled water.
2. ASD treatment in aqueous solution of 0.03 M $Na_2SiO_3.2H_2O$, 0.1 M β-glycerophosphate, 0.3M $C_4H_6CaO_4$, 0.036M NaOH and 3 g/l Ag nanoparticles. The solution is maintained at about 0±0.5° C., current density equal to 10 $mA/cm^2$, with a potential free to rise up to 300V. The ASD treatment is completed when the potential reaches 300 V and the current density drops to 20% of the initial value.
3. washing in distilled water and drying.

EXAMPLE 2

Preparation of the Metallic Substrates Obtained with the Treatment NITAgC (Silver Nitrate and L-Cysteine)

This treatment consists in the following operating conditions:
1. Superficial cleaning of grade II titanium sample, using an ultrasound tray for 3-5 minutes in acetone and for 3-5 minutes in distilled water.
2. ASD treatment in aqueous solution of 0.03 M $Na_2SiO_3.2H_2O$, 0.1 M β-glycerophosphate, 0.3M $C_4H_6CaO_4$, 0.036M NaOH, 0.004M $AgNO_3$ and 0.002M L-cysteine. The solution is maintained at about 0±0.5° C., current density equal to 10 $mA/cm^2$, with a potential free to rise up to 300V. The ASD treatment is completed when the potential reaches 300 V and the current density drops to 20% of the initial value;
3. washing in distilled water and drying.

EXAMPLE 3

Preparation of the Metallic Substrates Obtained with the Treatment NITGalC (Gallium Nitrate and L-Cysteine)

This treatment consists in the following operating conditions:
1. Superficial cleaning of grade II titanium sample, using an ultrasound tray for 3-5 minutes in acetone and for 3-5 minutes in distilled water.
2. ASD treatment in aqueous solution of 0.03 M $Na_2SiO_3.2H_2O$, 0.1 M β-glycerophosphate, 0.3M $C_4H_6CaO_4$, 0.036M NaOH, 0.004M $Ga(NO_3)_3$ and 0.006M L-cysteine. The solution is maintained at about 0±0.5° C., current density equal to 10 $mA/cm^2$, with a potential free to rise up to 300V. The ASD treatment is completed when the potential reaches 300 V and the current density drops to 20% of the initial value;
3. washing in distilled water and drying.

EXAMPLE 4

Preparation of the Metallic Substrates Obtained with the Treatment NITGalO (Gallium Nitrate and Oxalic Acid)

This treatment consists in the following operating conditions:
1. Superficial cleaning of grade II titanium sample, using an ultrasound tray for 3-5 minutes in acetone and for 3-5 minutes in distilled water.
2. ASD treatment in aqueous solution of 0.03 M $Na_2SiO_3.2H_2O$, 0.1 M of β-glycerophosphate, 0.3M $C_4H_6CaO_4$, 0.036M NaOH, 0.004M $Ga(NO_3)_3$ and 0.306M oxalic acid. The solution is maintained at about 0±0.5° C., current density equal to 10 $mA/cm^2$, with a potential free to rise up to 325V. The ASD treatment is completed when the potential reaches 325 V and the current density drops to 20% of the initial value;
3. washing in distilled water and drying.

EXAMPLE A

Preparation of the Metallic Substrates Obtained with the Process Disclosed in EP2037594-ASD Treatment with SUMNa This treatment consists in the following operating conditions:
1. Superficial cleaning of grade II titanium sample, using an ultrasound tray for 3-5 minutes in acetone and for 3-5 minutes in distilled water;
2. ASD treatment in aqueous solution of 0.03 M $Na_2SiO_3.2H_2O$, 0.1 M β-glycerophosphate, 0.3M $C_4H_6CaO_4$, 0.036M NaOH. The solution is maintained at about 0±0.5° C., current density equal to 10 mA/$cm^2$, with a potential free to rise up to 300 V. The ASD treatment is completed when the potential reaches 325 V and the current density drops to 20% of the initial value;
3. washing in distilled water,
4. treating the washed metallic substrate coming from the previous step with NaOH 5M at 60±2° C. for 2 hours;
5. washing in distilled water and drying.

Samples Analyses

The samples of the invention and the comparison samples have been examined and characterized by means of the following experimental procedures:

Scanning electron microscopy (SEM): analysis of the surface morphology (ZEISS-EVO 50 EP and ZEISS-EVO LS-15 Cambridge Stereoscan 360). For the observation of the cells grown on the samples the surface of each sample was coated with gold (Edwards, Sputter Coater S150B) and observation was performed under high vacuum conditions ($1 \times 10^{-5}$ mm Hg).

X-Ray Elemental Dispersion Spectroscopy (EDS): microanalysis (Oxford Inca Energy 200) was performed on 500× magnification on a portion of the sample having micrometric size;

Laser profilometry: the samples were subjected to 3 measurements of surface roughness performed with a laser prophilometer (UBM microfocus model 5600);

Thin film X-ray diffractometer (TF-XRD): the structure of the film was analyzed by means of a diffractometer (Philips PW 3710) with copper anode, setting 40 mA of current and a voltage of 40 kV. The thin film configuration was used for the present investigations.

superficial wettability analysis by means of static contact angle analysis (Dataphysics instruments Mod.OCA 15 plus; software 32 bit SCA20).The analysis was carried out in triplicate.

Inductively coupled plasma optical emission spectrometry (ICP-OES) allows to detect the release of Silver and Gallium from the surface following ASD treatment with AgNPS, NITAgC, NITGalO, NITGalC. Three samples for each treatment typology, had been maintained up to 21 days at 37° C. in 5 ml in PBS (phosphate buffer solution free from calcium ions) in Falcon probes under mild stirring (50 rpm). 5 ml PBS had been taken from each probe respectively after 1 day, 4, 7, 14 and 21 days of incubation and on each aliquot the inductively coupled plasma optical emission spectrometry analysis was carried out (ICP/OES Perkin Elmer Model ELAN-DCR-e).

Glow discharge optical emission spectrometry (GDOES) analysis was used as the analytical method to detect the Ag presence inside the coating produced when not detectable by EDS analysis.

Analysis of $TiO_2$ adherence: $TiO_2$ samples subjected to ASD having rectangular form (30 mm×50 mm) underwent flexion of 30 deg. On the folded surface of these samples a SEM analysis with a scanning electron microscope was carried out to evaluate the film damage.

In Vitro Biological Tests

3T3 cells (Murine Fibroblasts—ECACC) and Saos2 (osteoblasts obtained by human osteosarcoma—ECACC) were used for the cellular assays. 3T3 cells were cultured with Dulbecco Modified Eagle Medium (DMEM low glucose) with 584 mg/l of L-glutamine (PAA E15-806) containing 15% v/v of fetal bovine serum (FBS) (PAA E 15-104) in incubator (Heraeus, Hera cells) at 37° C. 95% relative humidity and 5% V/V $CO_2$. Saos2 cells were cultured in the culture medium "Mc Coys 5°" with 219.2 mg/l of L-glutamine (PAA e-15-823), containing 10% (V/V) of FBS in incubator (Heraeus, Hera cells) at 37° C. 95% relative humidity and 5% v/v $CO_2$.

sterilization: the samples previously passed in 100% ethanol were sterilized by u.v. exposure (235 nm, 30 min each side) under Class II biologic cowl (Esco AIR strem Class II BSC). Cellular seeding: the samples seeded with murine fibroblasts 3T3 were added to each sample in an amount of 6.1 μl ($3 \times 10^4$ cells) of the cellular suspension previously obtained by a tripsinization and successive dilution of 3T3 cellular cultures obtained in 75 ml flask (Nunc™). 1 ml DMEM was inserted on each well and samples were inserted into the incubator. For the osteoblasts cells 20 μl ($1.5 \times 10^4$ cells) of the suspension, previously obtained by tripsinization and successive dilution of the cellular culture in 75 ml flasks, were added to samples by means of a micropipette (NUNC™). 1 ml DMEM was inserted in each well.

The cellular viability and proliferation test was carried out by HPI (Hoechst 33342 and Propidium Iodide) on different samples incubated with the aforementioned different cellular lines: in particular:

the cultured samples with 3T3 cells underwent an HPI assay after 24 h and 48 h of cellular culture, whereas the Saos2 were analyzed with HPI after being cultured on samples for 48 h and 72 h. The procedure with HPI assay allows to analyze the effect produced on cells respectively by Hoechst 33342 which is able to penetrate the cellular membrane coloring dark blue (alive cells) or pink (apoptotic cells) visible by a fluorescence microscope; propidium iodide is able to penetrate inside damaged or even dead cells coloring DNA red. After removal of the culture medium from wells 10 μl of HPI were added to each well for 2 or 3 minutes in order to allow the formation of a stable bond of HPI with the cellular DNA. Finally the sample were observed at fluorescence microscope, by means of a filter with excitation wavelength equal to 365 nm and a wave length of 397 nm. The apoptosis was determined by an evident visualization of a nuclear fragmentation. The cellular counts was carried out by counting the alive apoptotic and dead cells on different six random zone of each sample by 40× magnification. Two different samples were used for each treatment at every time point (n=12).

The morphology adhesion evaluation of Saos2 cell was made after 48 and 72 h from seeding. After removal of cellular supernatant, the samples were mildly washed in PBS (phosphate buffer) and afterwards were incubated in glutaraldehyde on PBS for 45 minutes. The incubation in glutaraldehyde fixed the cells by crosslinking proteins present on their cellular membranes. The cells were then gently washed three times in sterile distilled water in order to remove any trace of glutaraldehyde. The cleaned samples were dehydrated in ethanol solution of increasing concentrations (25%, 50%, 75%, 90% for two times). After dehydration, the samples were freeze dried overnight, mounted on SEM stabs, sputter coated with platinum (Quorum QT150 TS) and analyzed with SEM.

Saos2 cellular spreading analysis with Phalloidin Assay: The samples after being cultured for respectively 48 and 72 h from seeding Saos2 cells, previously incubated in a 3.7% formaldehyde solution in PBS, were then incubated with a solution of Phalloidin-Rhodamine (Sigma, TRITC P1951). Phalloidin assay is useful for assessing cellular spreading and the disposition of actin filaments thereof. The samples were observed at fluorescence microscope by using a red filter at 540 nm.

DAPI (4,6 diamidin-2-phenyl-indole) assay allows to perform cellular nuclei DNA coloring, detectable at fluorescence microscope, while maintaining unaltered the cellular membranes. DAPI solution is added to the incubated samples with Phalloidin to identify the cellular nuclei, the cytoskeleton thereof was already labeled and visible thanks to Phalloidin.

Antibacterial Activity

A preliminary assessment of the antibacterial activity of the surface modified metallic substrates according to the present invention and the ability thereof to limit bacterial adhesion (no fouling activity) was realized by incubating with different both gram negative and gram positive bacterial strains. As far as gram positive bacteria are concerned bacterial strains *Streptococcus Mutans* (CCUG 35176) and *Streptococcus Epidermidis* (RP62A Department of Microbiology, Dublin, Ireland) were used. Insofar as gram negative bacteria are concerned *Escherichia Coli* RB (Istituto Zooprofilattico Pavia, IT) was used. *Escherichia Coli* was cultured overnight in LB (Luria Bertani) broth (Difco Detroit, Mich., USA) under aerobic conditions at 37° C. using a basculating incubator (New Brunswick Scientific Co., Edison N.J. USA). *Streptococcus Mutans* bacteria were cultured in Brain Heart Infusion (BHI-BD Difco, Frankil Lakes, N.J., USA) BY ADDING 10% V/V of horse serum (Oxoid, Rodano, Milan, Italy), for growth stimulation; finally bacteria were incubated for under anaerobic conditions at 37° C. *Streptococcus Epidermidis* bacteria were grown overnight in tryptic soy broth (TSB) (Difco, Detroit, Mich., USA), under aerobic conditions at 37° C. using the aforementioned basculating incubator.

For the antibacterial activity analysis the samples were incubated with an aliquot having a determined concentration of the different cellular suspensions for 3 and 24 h without stirring at 37° C. As control culture, wells of plastic material were used and incubated at the same operating conditions and concentrations as the samples to be tested. At the end of the incubation it was possible to determine the bacterial growth present on the sample surface as ratio of bacterial growth on the sample/control cells (considered as 100%) by means of a process of serial dilutions and agar plates cultures. Every experiment was carried out in triplicate and the data are expressed as average values±standard deviation.

As far as the bacterial adhesion evaluation is concerned, the samples were incubated for 3 h in a bacterial solution at known concentrations. This solution was deposited on the sample to cover the whole surface thereof. At the end of the incubation the samples were washed in a suitable buffer and then bacteria adhered to the surface were mechanically removed by stirring (Vortex for 5 minutes) and suspended in a Ringer solution. By carrying out a process encompassing serial dilutions and agar plates cultures, it was possible to determine the percentage of bacteria present on the sample surface as ratio of bacterial growth of the sample/control cells (considered as 100%).

Results

Figure 1B:
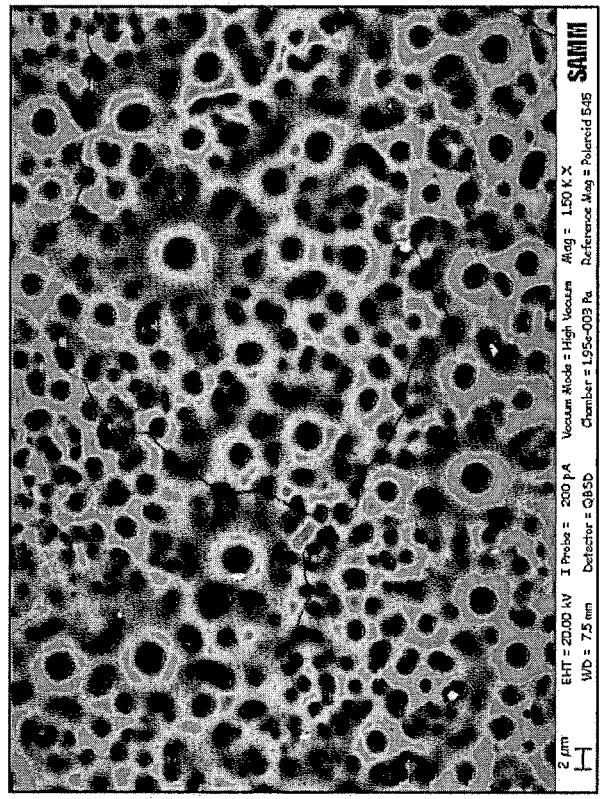
Figure 1C:
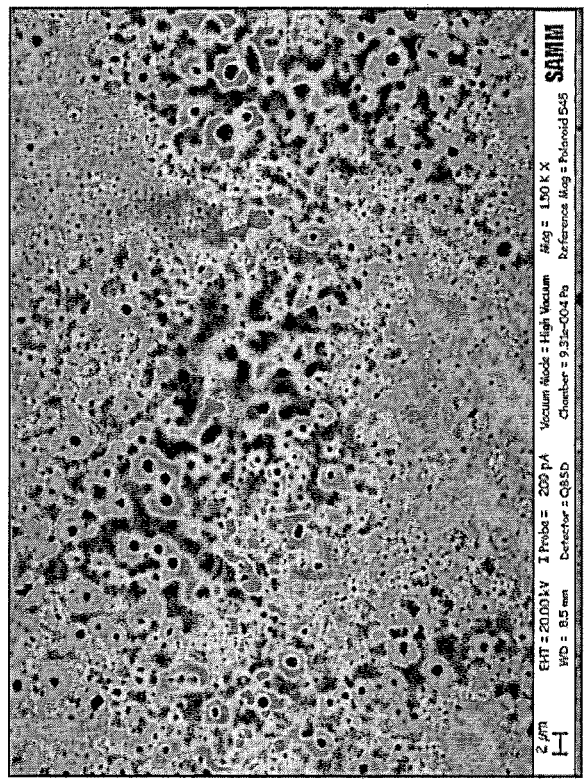
Figure 1D:
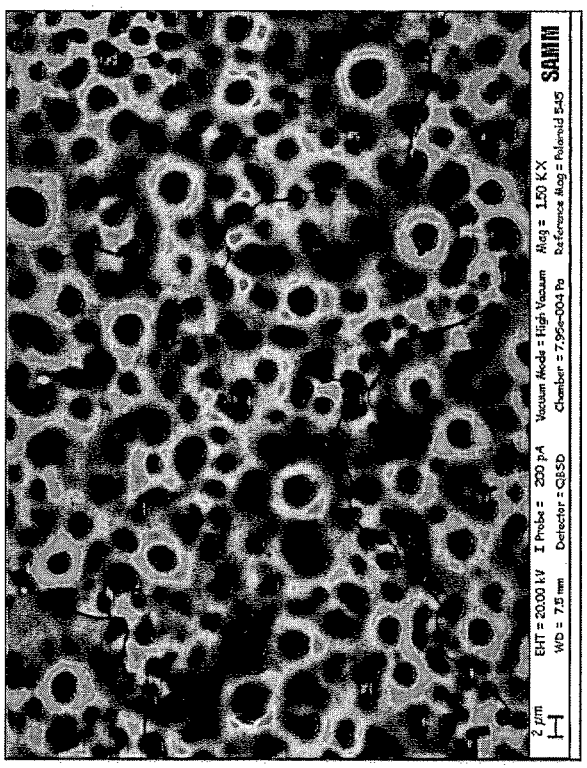
Figure 1E:
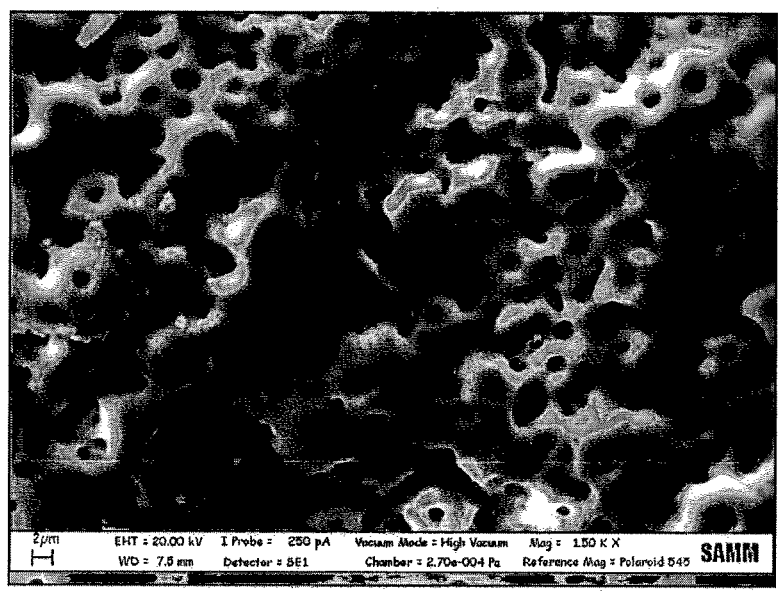
Figure 2B:
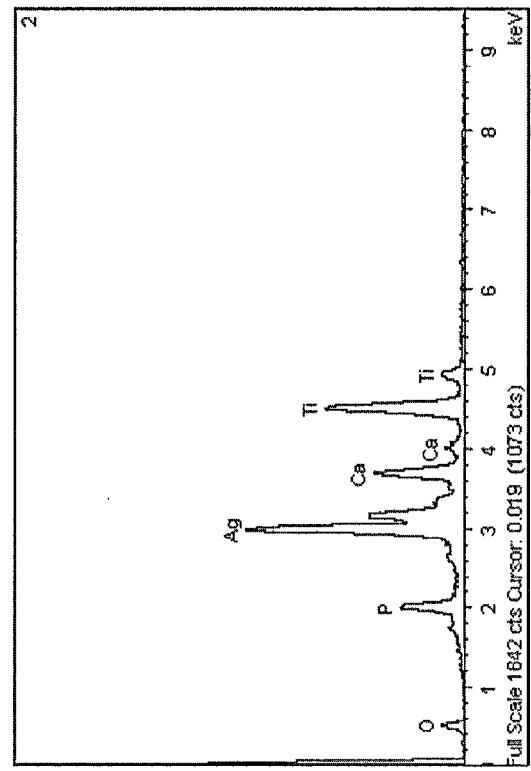
FIGS. 2A-2F: EDS microanalysis undergoing ASD treatments with respectively: A) AgNPs, (A.1 particle details), B) NITAgC, C) NITGalC, D) NITGalO, and E) SUMNa (Control).
Figure 2A:
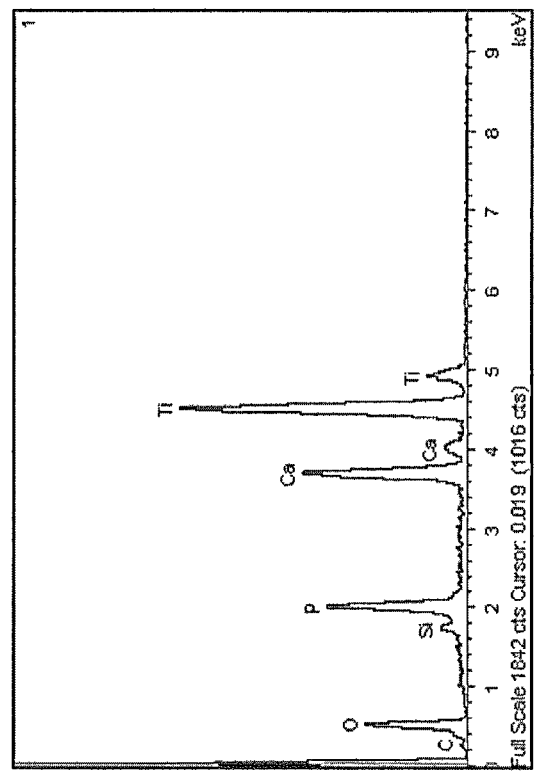
Figure 2D:
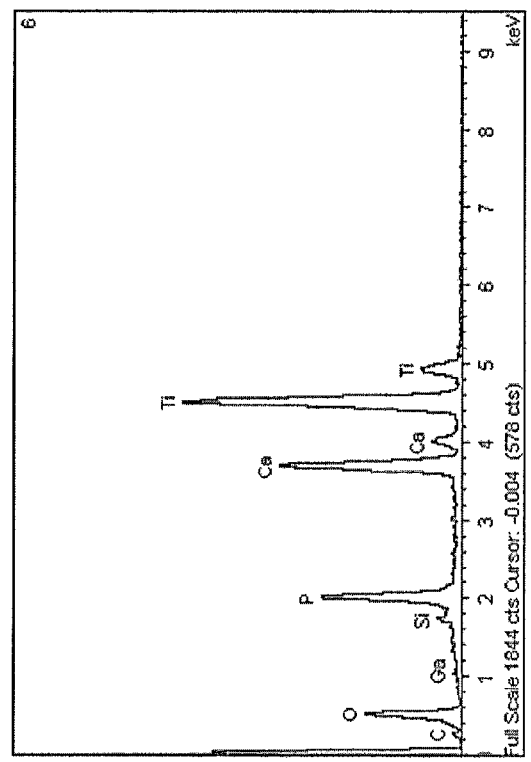
Figure 2C:
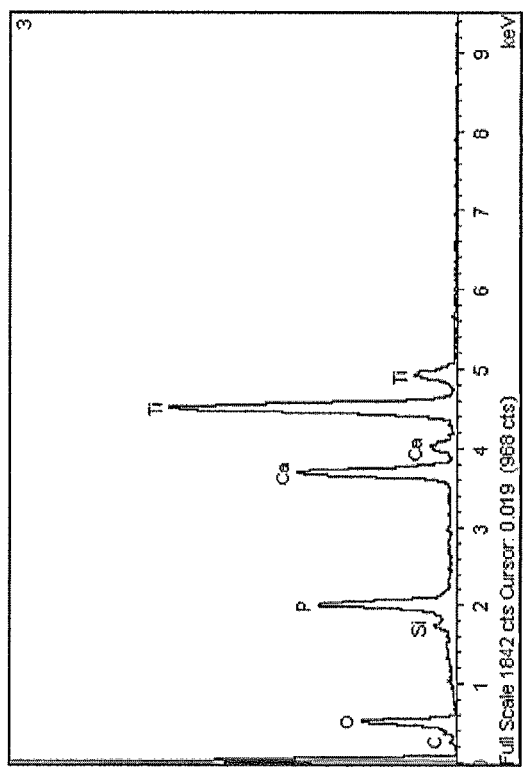
Figure 2F:
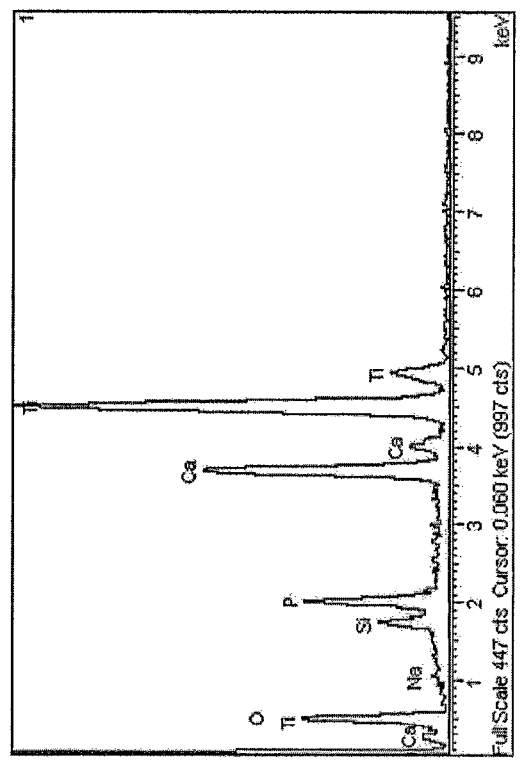
Figure 2E:
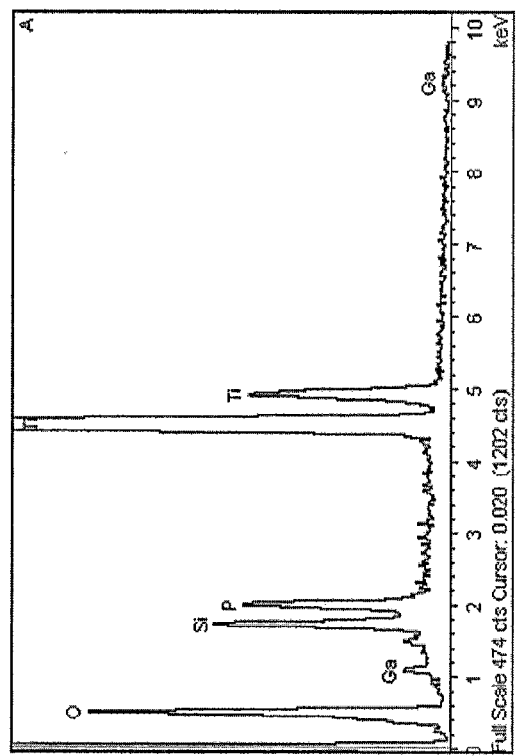
Figure 3:
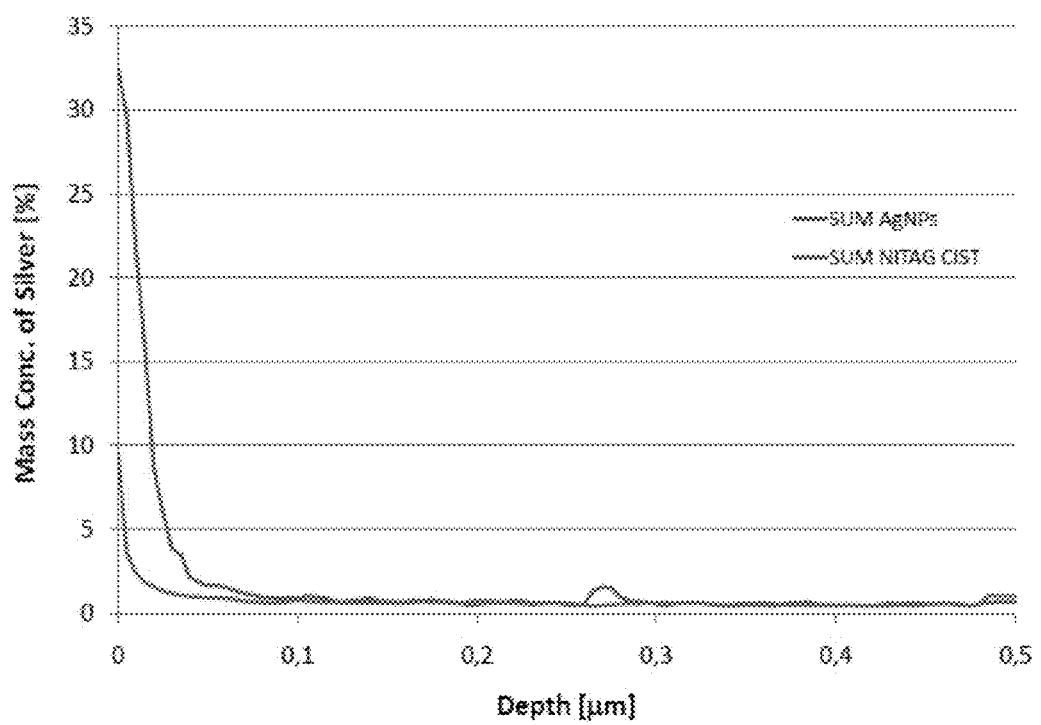
FIG. 3: GDOES analysis Ag concentration vs. Oxide depth (thickness) in sample undergoing ASD treatments with respectively: AgNPs and NITAgC.
Figure 4A:
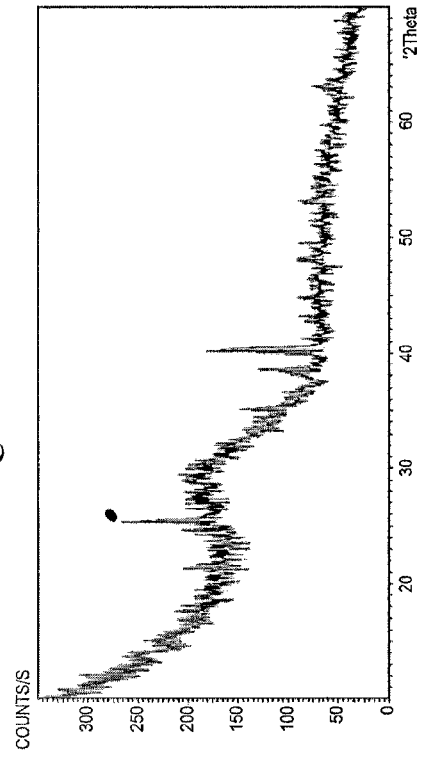
FIGS. 4A-4E: TF-XRD spectra of samples undergoing ASD treatment with respectively: A) AgNPs, B) NITAgC, C) NITGalC, D) NITGalO, and E) SUMNa (Control) wherein . indicates the anatase peak and 0 indicates the rutile
Figure 4C:
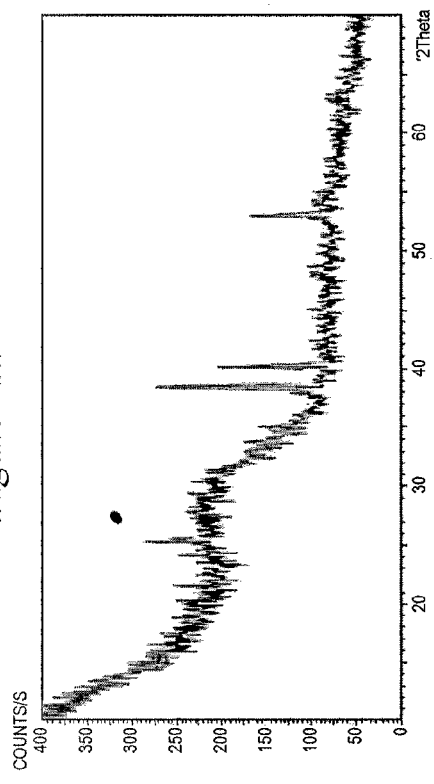
Figure 4B:
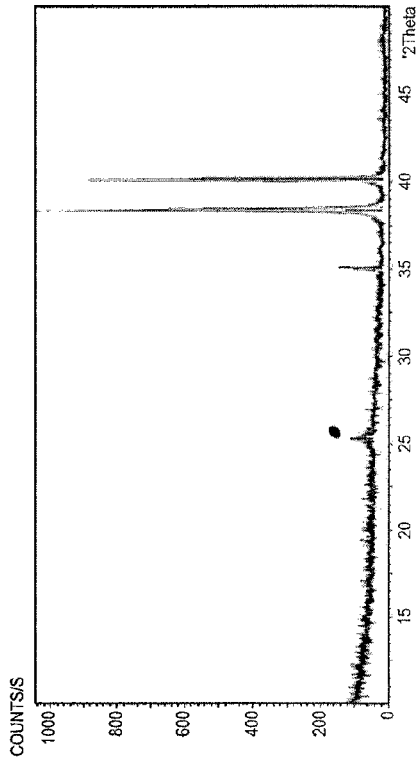
Figure 4D:
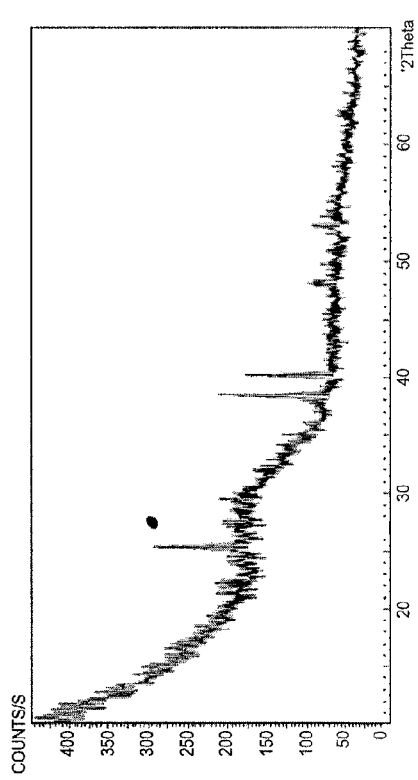
Figure 4E:
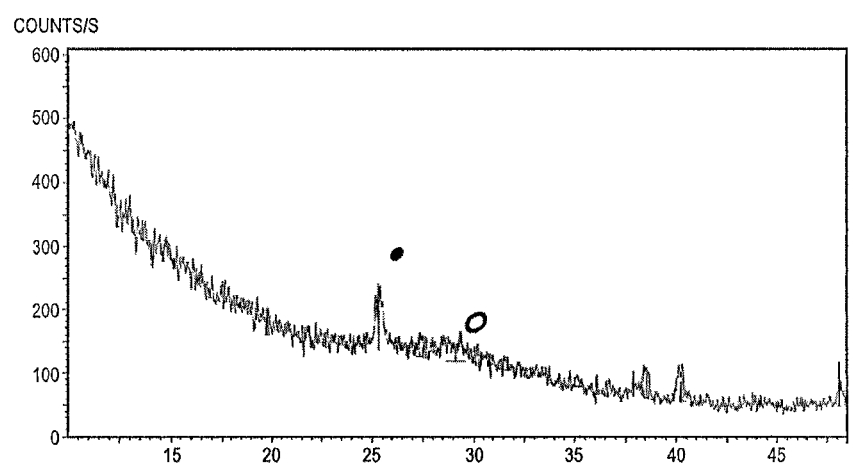
Figures 1, 13A:
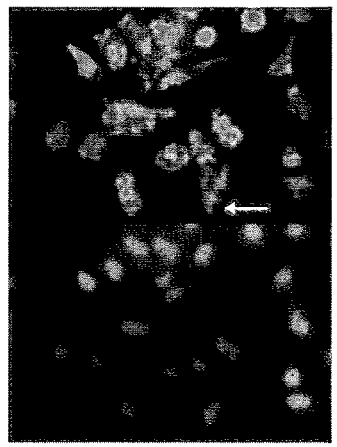
FIGS. 13A-1 - 13E-2: fluorescence pictures of Phalloidin staining (red) and DAPI staining (blue) of Saos2 cell after 48 h (a) and 72 h (b) of cell culture on materials prepared by ASD treatment with respectively: A) SUMNa (control), B) AgNPs, C) NITAgC, D) NITGalC, E) NITGalO. In the top image of each picture (a) and (b) the cellular cytoskeleton is visible, the arrows indicate the presence of focal points of contact among cells.
Figures 2, 13A:
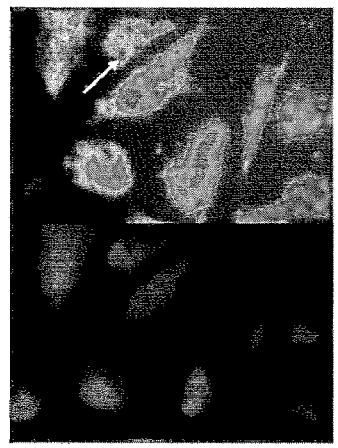
Figures 1, 13B:
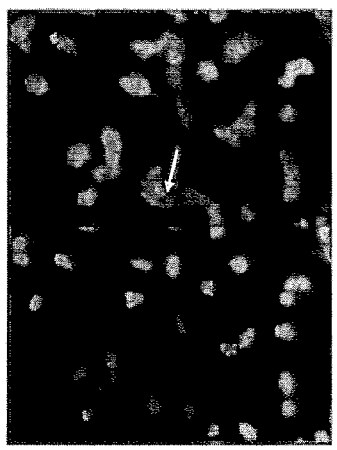
Figures 2, 13B:
Figures 1, 13C:
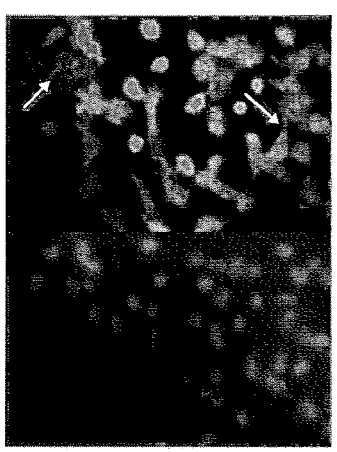
Figures 2, 13C:
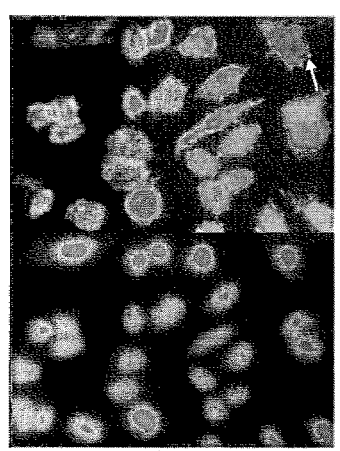
Figures 1, 13D:
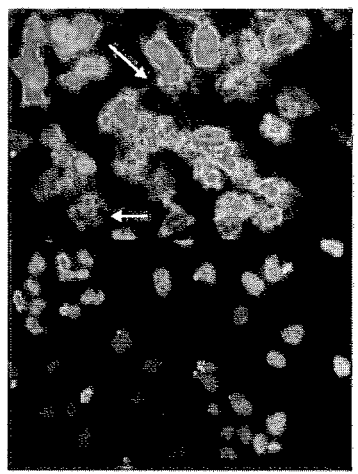
Figures 2, 13D:
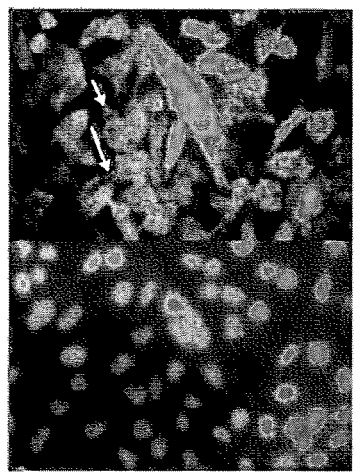
Figures 1, 13E:
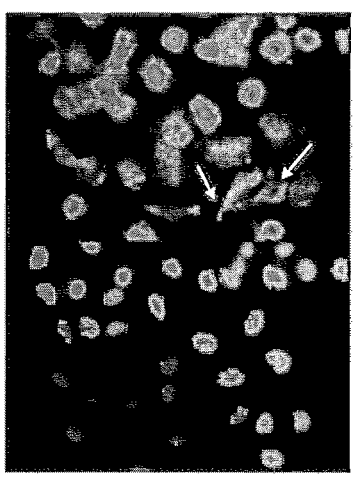
Figures 2, 13E:
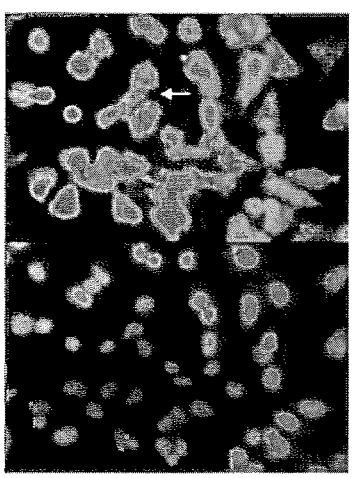
Figure 14B:
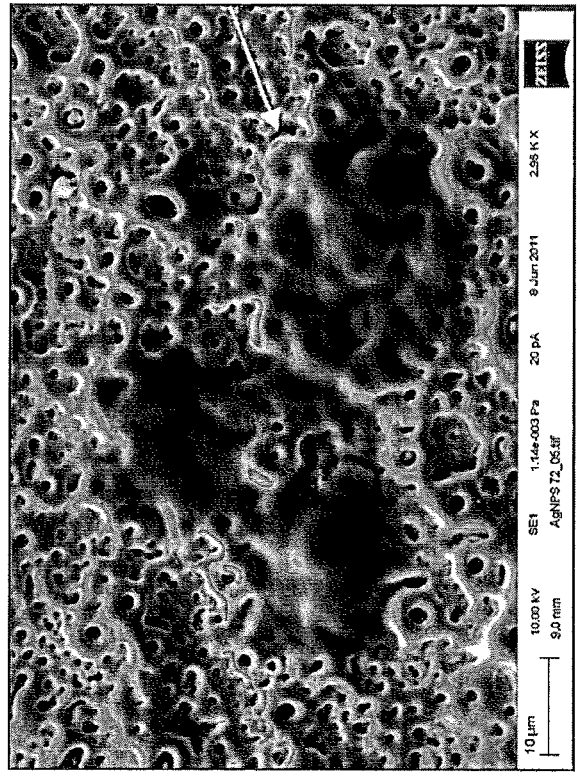
FIGS. 14A-14E: SEM pictures of Saos 2 cells after they had been cultured for 72 h on samples prepared by ASD treatment with respectively: A) AgNPs, B) NITAgC, C) NITGalC, D) NITGalO, and E) SUMNa (Control), wherein the arrows reported in FIG. 14B and D evidence some cellular cytoskeleton details, confirming that the cells adapt themselves to the porous morphology of the surface modified metallic substrates of the invention.
Figure 14A:
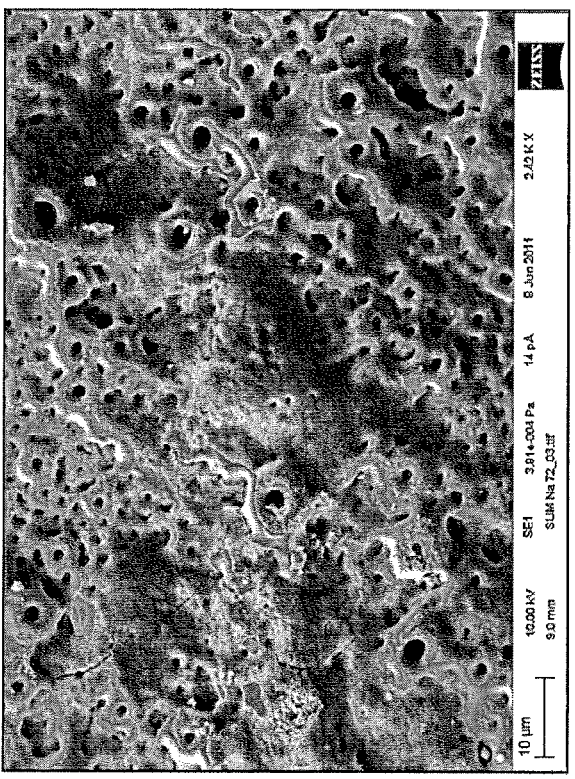
Figures 14C, 14D:
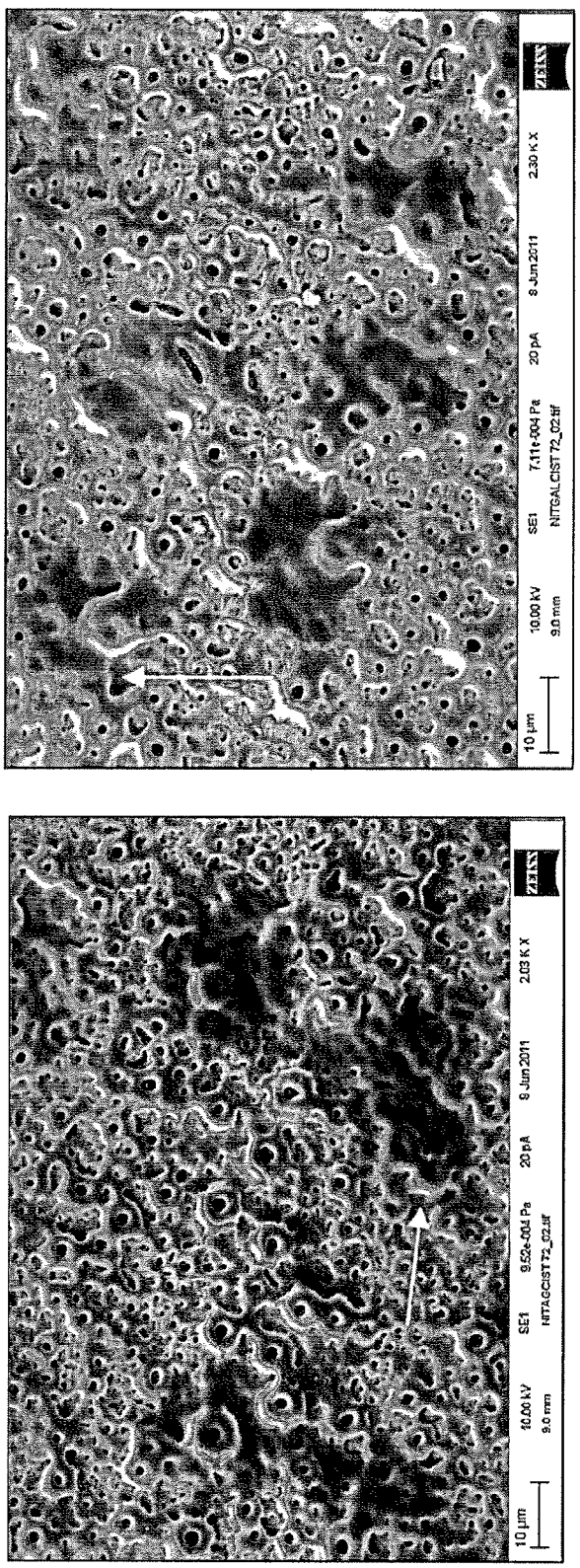
Figure 14E:
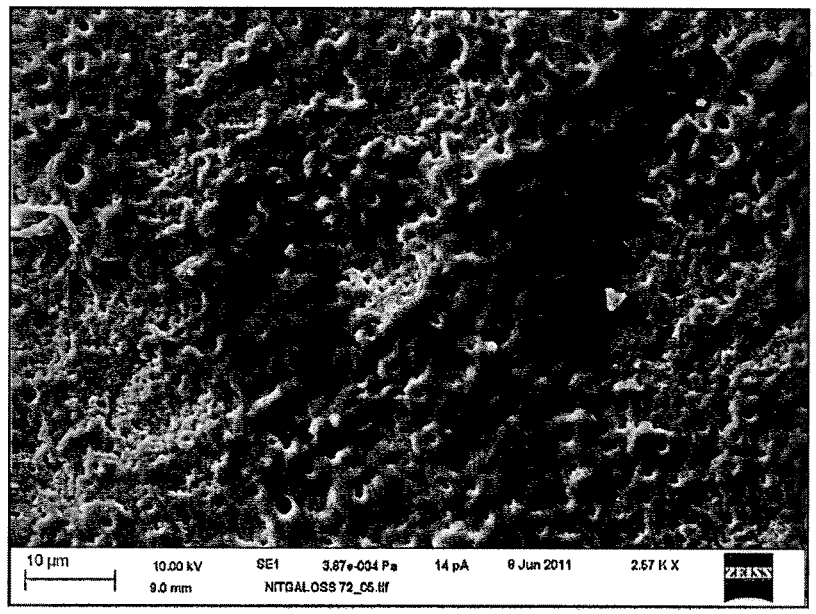

The SEM analysis of the superficial morphology showed that AgNPs, NITAgC and NITGalC presented a homogeneous coating with roundish pores of micrometric size (FIG. 1A-C) very similar to those obtained with the control (SUMNa) of FIG. 1E. As far as NITGalO (FIG. 1.D) the coating is less homogenous, and characterized by pores having smaller size than those of the other samples and of the control. In all case no $TiO_2$ delamination was observed in all samples. EDS analysis highlights the presence of calcium, silicon and phosphorus on all the samples surface with the exception of NITGalO sample, not reporting the calcium peak probably because of the limited presence of this element in NITGalO sample surface (FIG. 2.A-E). EDS analysis of NITGalO and NITGalC confirmed the presence of Gallium on both surfaces (FIGS. 2.C and 2.D) and the silver presence on AgNPs surface, but not the presence of this element on NITAgC surface (FIG. 2B). The presence of this element on this surface was however evidenced from GDOES analysis (FIG. 3A). This analysis was also useful to demonstrate the presence of Ag in the outermost layers of both AgNPs and NITAgC samples surfaces within 150 μm thickness.

XRD analysis underlines that the titanium oxide present in the surface after ASD treatments show in all cases the anatase crystal form at contact angle $\theta=25°$ (FIG. 4.A-E). In particular on the NITGalO sample surface XRD spectrum detects a previous crystal structure before the amorphous phase present in all other treatments. In fact this XRD spectrum results to be the least noisy (see FIG. 4.D). The XRD spectrum of SUMNa (control) (FIG. 4.E) reveals also the presence of the crystallographic structure of rutile besides that of anatase.

The presence of anatase in all samples represents a positive advantage since anatase possesses important catalytic properties that in vitro stimulate hydroxyapatite crystals nucleation increasing the in vivo performances, associated with a decrease in the bacterial adhesion without compromising the eukaryotic cellular activity.

Figure 5A:
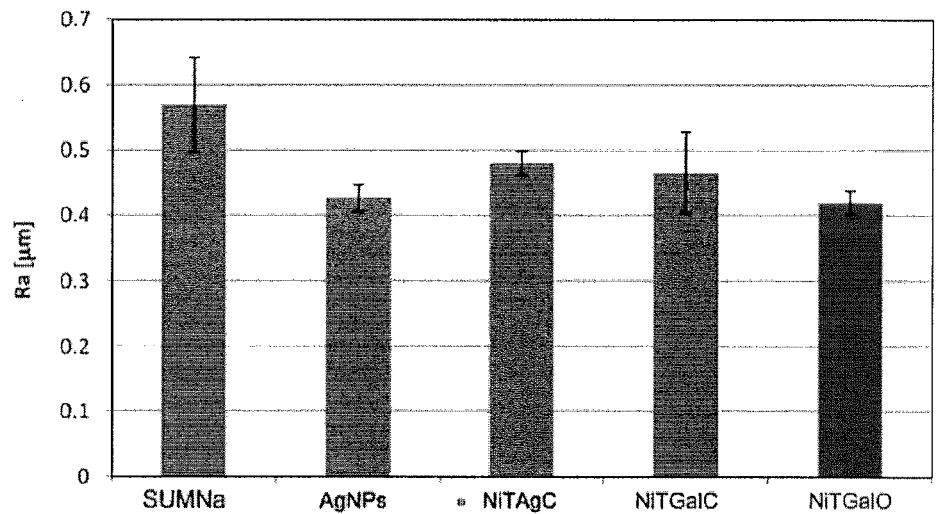
FIGS. 5A-5C: Profilometric analysis A) $R_a$ parameter, B) $R_t$ parameter, C) $R_{max}$, parameter of the samples subjected to ASD treatment with respectively: AgNPs, NITAgC, NITGalC, NITGalO and SUMNa (control).
Figure 5B:
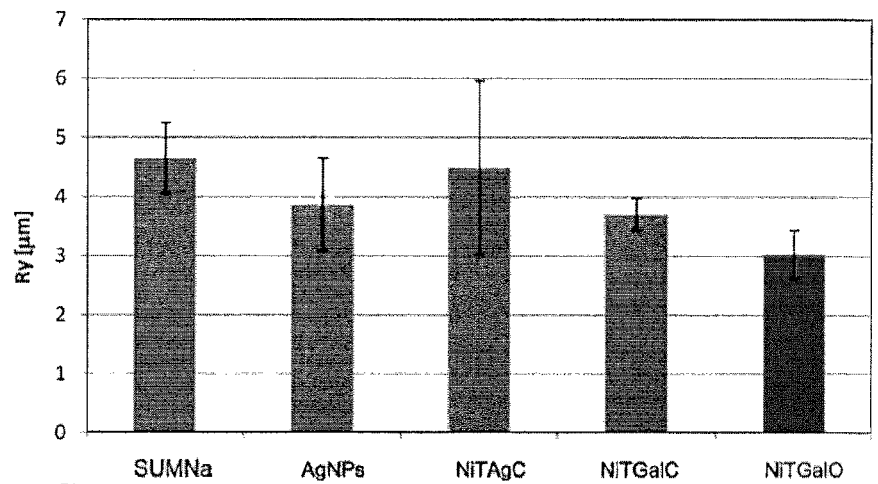
Figure 5C:
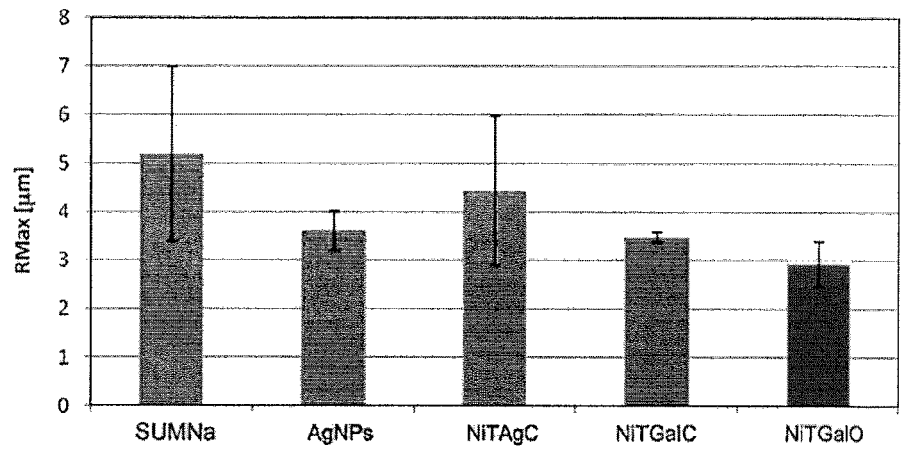

Laser profilometry evidenced a light decrease in rugosity $R_a$ if compared to the control (SUMNa) (FIG. 5.A). A not significant reduction of $R_{max}$ and $R_y$ of the samples according to the invention in comparison with control (SUMNa), in particular the treatment with NITAgC, as well as the control material shows high dispersion of the data (FIGS. 5.B, 5.C). It was widely demonstrated in literature that the superficial roughness of a material has a beneficial effect in terms of cellular differentiation and proliferation. The profilometric analysis reports that all samples as well as the control (SUMNa) possess a nanoroughned surface.

The wettability analysis was conducted to verify the hydrophilic properties of the samples of the invention. The results reported in FIG. 6 highlighted that all samples were more hydrophilic if compared to not treated titanium surface, whose surface shows a hydrophobic feature (FIG. 7.A [$\theta \approx 92°$]) The control sample (SUMNa) results to be highly hydrophilic with a static contact angle so small that it is practically impossible to determine (FIG. 7B). All the other samples according to the invention (AGNPs, NITAgC, NITGalC and NITGalO) showed hydrophilic surface below the known Berg's soil ($50°<\theta<55°$), above said soil the plasmatic proteins are denatured when absorbed on the surface. (See FIGS. 6 and 8.A-D). Hydrophilic surfaces may result advantageous since they are more resistant to bacterial adhesions than the hydrophobic surfaces.

Figure 9:
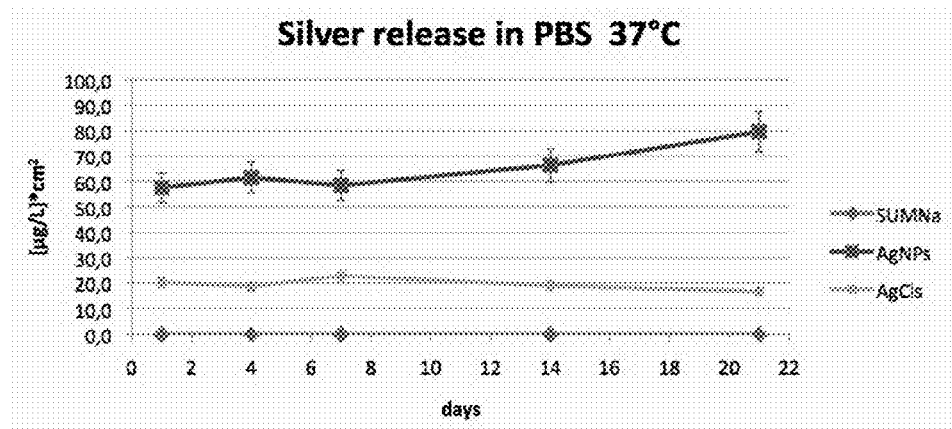
FIG. 9A: Ag release from the sample prepared by ASD with respectively: AgNPs and NITAgC in comparison with SUMNa after 1 day, 4 days, 7 days 14 and 21 days in PBS.
FIGS. 9B and 9C: Ga release from the sample prepared by ASD with respectively: B) NITGalO and NITGalC after 1day, 4 days, 7 days 14 and 21 days in PBS.
Figure 9:
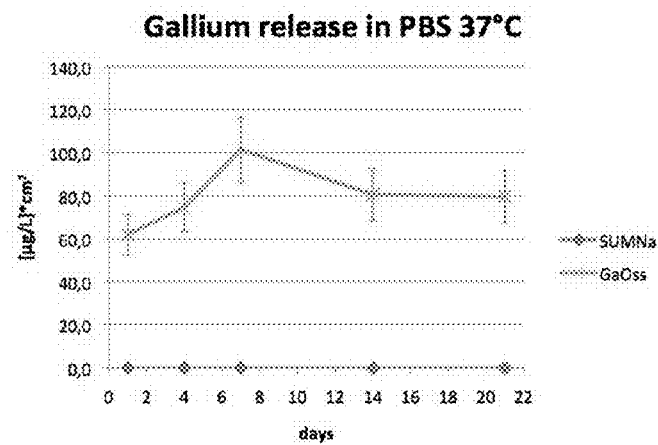
Figure 9:
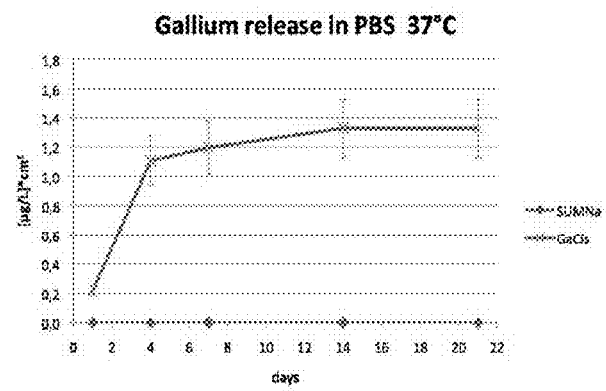
Figure 10B:
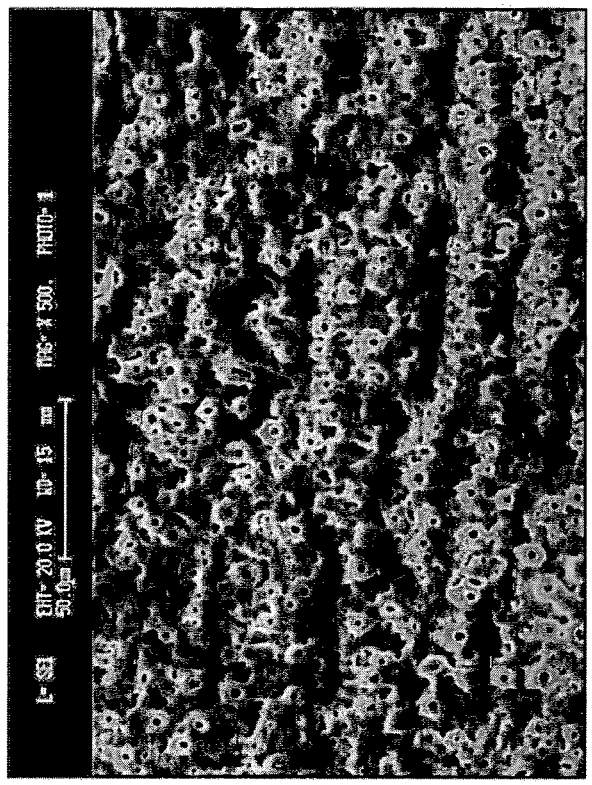
FIGS. 10A-10D: SEM Pictures (500X magnification) of 3 points flexion test carried out on samples that underwent ASD deposition with respectively: A) AgNPs, B) NITAgC, C) NITGalC and D) NITGalO.
Figure 10A:
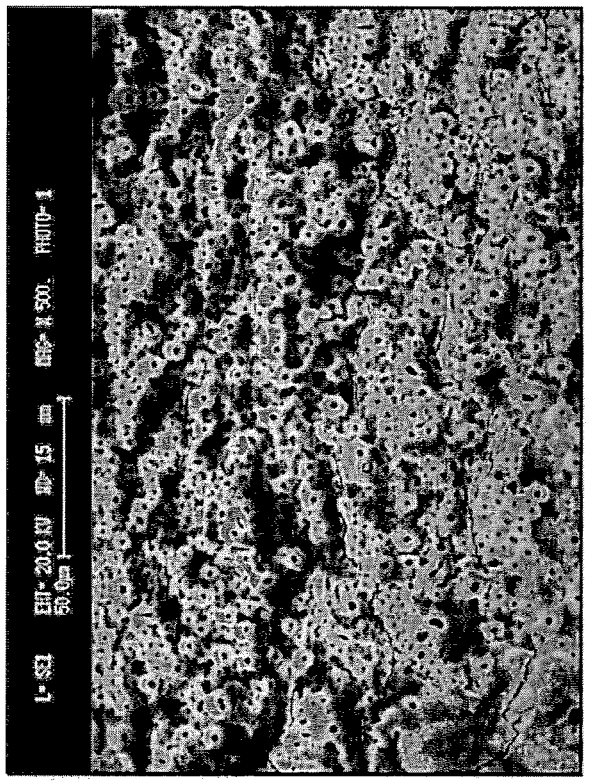
Figure 10D:
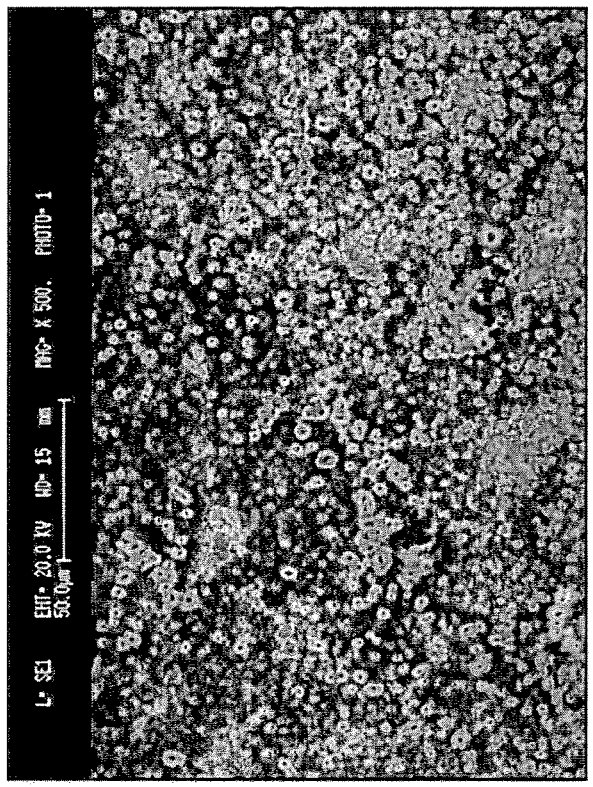
Figure 10C:
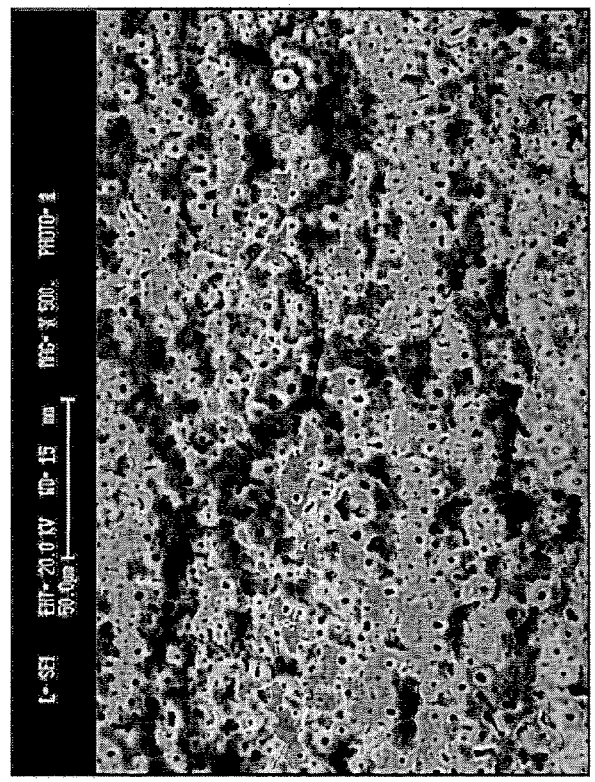

ICP/OES analysis allowed to evaluate the Ag and Ga release from the samples of the invention (FIG. 9.A-C). For both AgNPs and NITAgC samples, a constant silver release occurred from the first to the seventh day, thereby slightly increasing from the seventh up to the 21$^{st}$ day for the AgNPs sample. As far the NITAgC sample is concerned, the Ag release occurred almost completely within the first day, without a significant increase from the seventh to the 21$^{st}$ day. The release degree was lower for NITAgC (AgC is in the FIG. 9A) if compared to AgNPs sample. However in both cases the release was limited (max 80 μg/l per cm$^2$ of immersed sample). As far as the gallium release is concerned, the release from the NITGalO sample occurred within the first week thereby stabilizing up to a value of about 80 μg/l per cm$^2$ of immersed sample (FIG. 9.B). The release of the antibacterial agent from NITGalC occurred from the first up to the fourth day thereby remaining constant up to the 21$^{st}$ day. In this case the total release amount was extremely reduced (max 1.5 μg/l per cm$^2$ of immersed sample in 21 days—FIG. 9.C).

The 3 points flexion test showed that notwithstanding the imposed limit condition of flexion (30 deg) all samples remain adherent to the surface of the underlying titanium, not showing any delaminated zone free from the titanium oxide. SEM analyses evidenced only some small cracks in the oxide however not showing any delamination and not prejudicing the resistance of titanium oxide coating.

Figure 11:
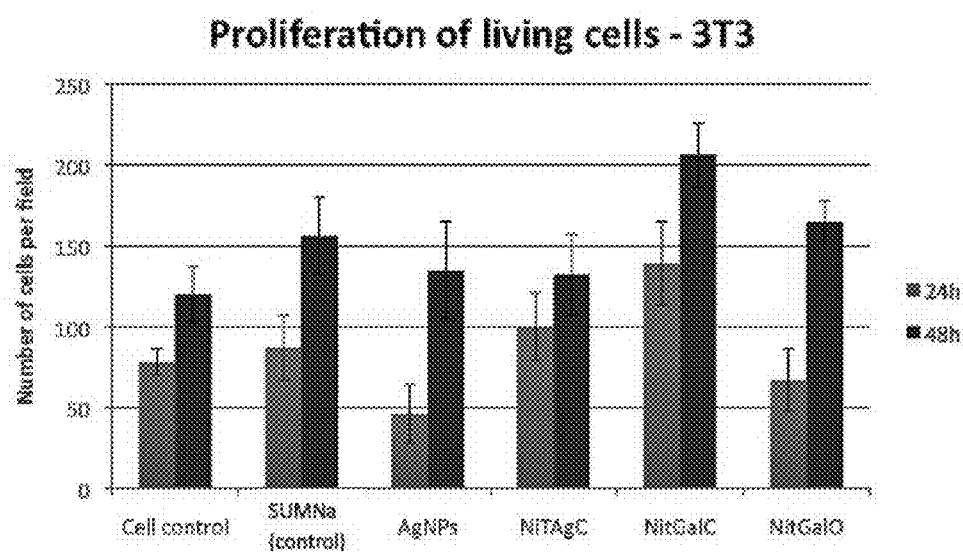
FIG. 11: graphic illustrating: viability performed with HPI staining test carried out after 24 and 48 h of cell culture on samples prepared by ASD deposition with respectively: AgNPs, NITAgC, NITGalC, NITGalO and SUMNa (control).

The graphic relative to the study of cellular activity of fibroblast cells 3T3 (FIG. 11) demonstrated that all samples of the invention and also SUMNa (control) showed a cellular activity after 48 h culture higher than that of the control (cells seeded on plastic wells). Any cytotoxic effect was excluded on the eukaryotic cells induced by the antibacterial samples of the invention.

Figure 12:
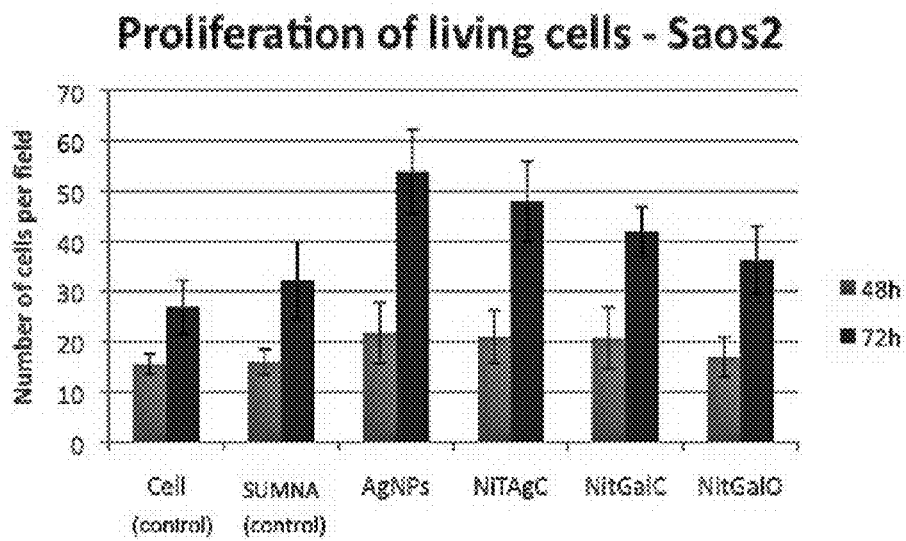
FIG. 12: graphic illustrating: Saos2 osteoblasts viability performed with HPI staining test after 48 and 72 h of cell culture on samples prepared by ASD treatment with respectively: AgNPs, NITAgC, NITGalC, NITGalO e SUMNa (control).

Neither any cytotoxic effect on osteobalsts of the line Saos2 was detectable in the antibacterial sample of the invention after 48 and 72 h culture. All samples showed an increase in cellular viability if compared to those seeded in plastic wells after 72 h culture. In particular the samples AgNPs, NITAgC and NITGalC were those presenting the best cellular proliferation even better than that obtained with SUMNa (control) sample (FIG. 12).

The Saos2 cells after 48 and 72 h cultures resulted to adhere very well on the samples of the invention with an important cytoplasmatic component characterized by an eccentric nucleus. The cellular cytoskeleton appeared more and more organized passing from 48 h to 72 h cultures. In the first culture 48 h the cellular cytoskeleton adapted itself to the roundish structure of the pores present in the surface of the samples of the invention and subsequently (72 h) an optimal organization of the cytoskeleton was observed, characterized by the presence of oriented actin filaments that sometimes concurred with the formation of filopodia and focal contact points among the cells (FIGS. 13.A-E)

The SEM pictures of Saos2 osteoblasts cells after 72 h culture reported in FIGS. 14 A-E illustrated that cellular morphology of these cells on the samples of the invention resulted completely spread on the surface of these samples; the cytoskeleton adapted itself so well to the porous morphology of the surface of the samples of the invention that it resulted very difficult the individuation of the cells, since they perfectly followed the pores profiles. No relevant difference were observed between the sample of the invention and the control (SUMNa).

The above results of biologic characterization demonstrated that no sample of the invention exerted a cytotoxic effect on analyzed eukaryotic cells and in some cases even an increase in cellular proliferation was observed in comparison with control (SUMNa).

Figure 15B:
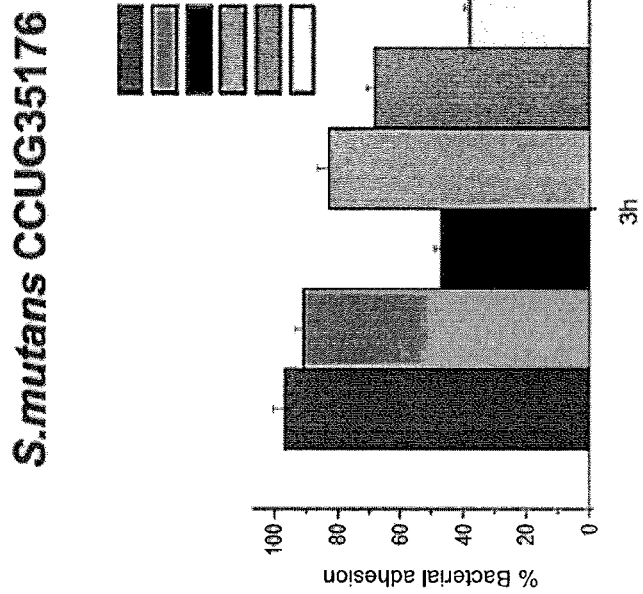
FIG. 15B: cellular adhesion of *Streptococcus Mutans* CGUG 35176 after 3 hours incubation with a material not undergoing ASD deposition (Ti II) and materials undergoing ASD with respectively: SUMNa, AgNPs, NITAgC, NITGalC and NITGalO. The values are reported as % of adhered bacteria on small disks made of the above material in comparison with those adhered on plastic support (positive control).
Figure 15A:
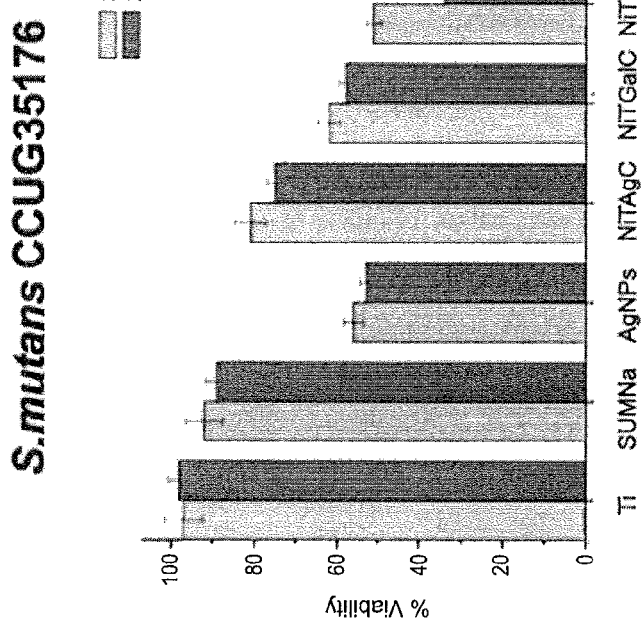
FIG. 15A: cellular viability of *Streptococcus Mutans* CGUG 35176 after 3 and 24 h incubation on sample not undergoing ASD treatment (Ti) and sample undergoing ASD treatment with respectively SUMNa, AgNPs, NITAgC, NITGalC and NITGalO. The values are reported as % of grown bacteria on small disks made of the above material in comparison with those grown on plastic support (positive control).

The results of microbiologic characterization highlighted a potential antibacterial effects exerted by the sample of the invention on all the tested bacterial strains. In particular from the graphic of FIG. 15.A reporting the cellular viability of *Streptococcus Mutans* after respectively 3 and 24 h culture on the different sample surfaces illustrated that a marked reduction of the samples according to the present invention in bacterial viability was observed in comparison with SUMNa (Control) and not treated titanium surface after 3 h. Moreover as the incubation time went by (24 h), a further reduction of bacterial viability was observed. The above data therefore demonstrated that the sample according to the invention in comparison with untreated titanium surface and SUMNa sample exhibit an increase in antibacterial activity. FIG. 15B shows that all samples and more in particular AgNPs, NITGalC and NITGalO have an important reduction in bacterial adhesion after 3 h incubation.

Figure 16B:
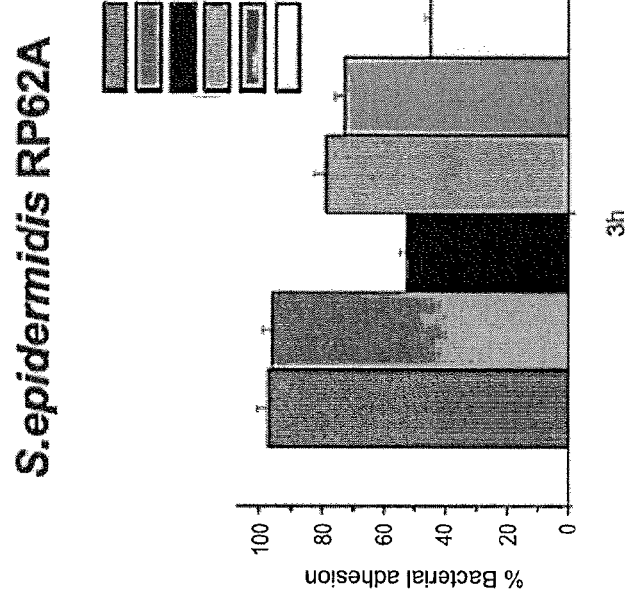
FIG. 16B: cellular adhesion of *Streptococcus Epidermidis* RP62A after 3 hours incubation with a material not undergoing ASD (Ti II) and materials undergoing ASD with respectively: SUMNa, AgNPs, NITAgC, NITGalC and NITGalO. The values are reported as % of adhered bacteria on small disks made of the above material in comparison with those adhered on plastic support (positive control).
Figure 16A:
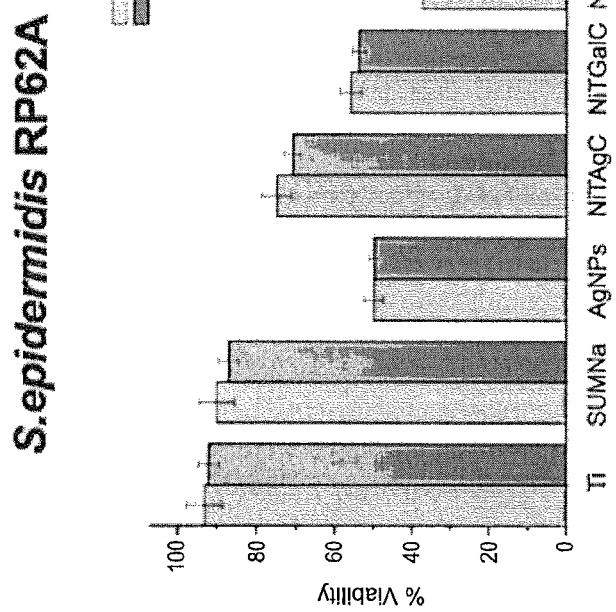
FIG. 16A: cellular viability of *Streptococcus Epidermidis* RP62A after 3 and 24 h incubation with a sample not undergoing ASD (Ti) and samples undergoing ASD with: respectively SUMNa, AgNPs, NITAgC, NITGalC and NITGalO. The values are reported as % of grown bacteria on small disks made of the above material in comparison with those grown on plastic support (positive control).

An analogous behavior was observed also for the other gram negative bacterium (*Stafilococcus Epidermidis* wherein a marked reduction of bacterial viability both after 3 h and 24 h culture and of bacterial adhesion after 3 h culture, of the surface modified samples according to the invention as it is clearly evident from FIG. 16.A-B.

Figures 17A, 17B:
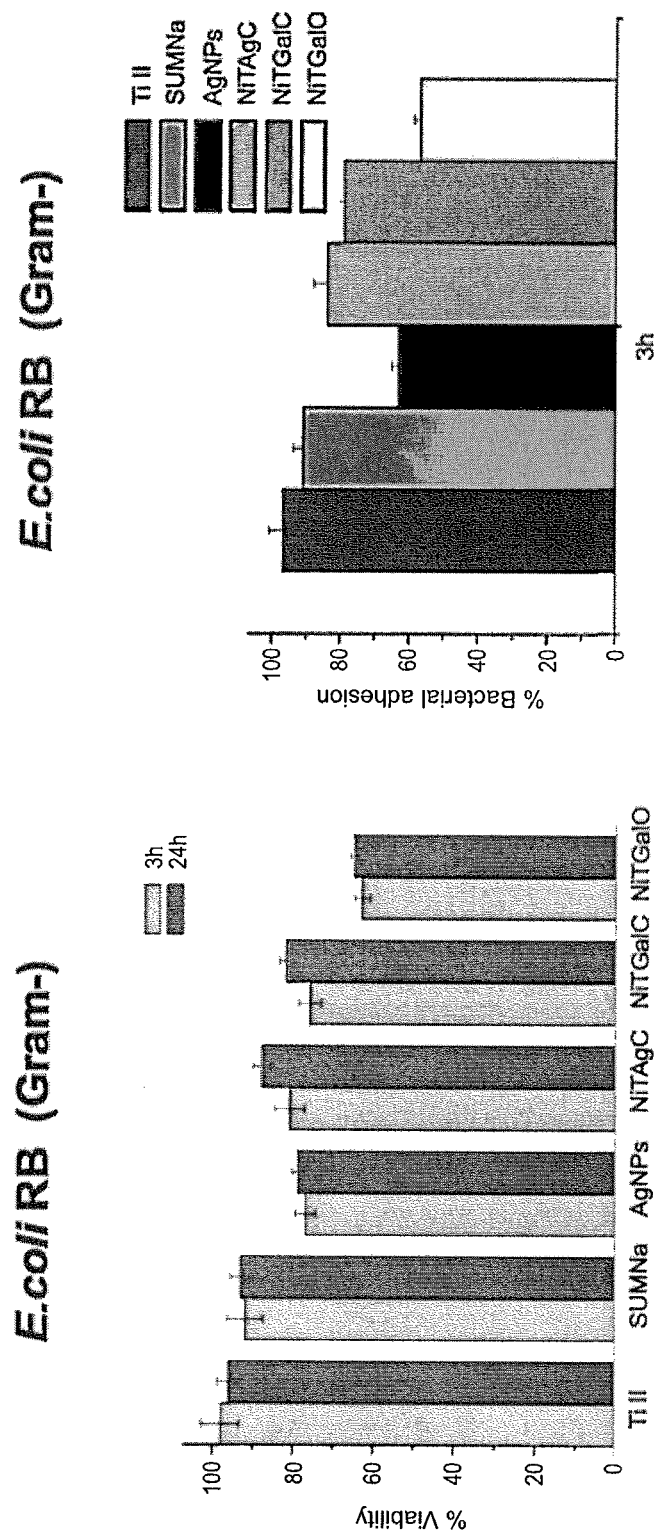
FIG. 17A: cellular viability of *Escherichia Coli* RB after 3 and 24 h incubation with material not undergoing ASD (Ti) and materials undergoing deposition with respectively: SUMNa, AgNPs, NITAgC, NITGalC and NITGalO. The values are reported as % of grown bacteria on small disks made of the above material in comparison with those grown on plastic support (positive control).
FIG. 17B: cellular adhesion of *Escherichia Coli* RB after 3 h incubation with material not undergoing ASD (Ti II) and material undergoing deposition with respectively SUMNa, AgNPs, NITAgC, NITGalC and NITGalO. The values are reported as % of adhered bacteria on small disks made of the above material in comparison with those adhered on plastic support (positive control).

The sample of the invention resulted effective in reducing bacterial viability after 3 and 24 h and adhesion after 3 h culture of *Escherichia Coli* (FIGS. 17.A-B).

It follows therefore that the surface modified metallic substrates of the invention resulted able to improve osteointegration stimulating the cellular proliferation, the mineralization process while contemporaneously imparting an antibacterial effect.

Moreover, as also pointed previously, the above features are obtained without the necessity to perform an alkaline etching after ASD, as it occurs with the metallic substrates disclosed in EP2037594, to advantage of the process economy.

The surface modified metal substrates of the invention are in particular useful in the preparation of not cemented prosthesis components and dental implants.

The invention claimed is:

1. A process for preparing a substrate of a metal selected from the group consisting of titanium, tantalum, titanium alloys and tantalum alloys, modified by anodic spark deposition (ASD) on the surface thereof of a microporous and nano-roughened layer of the oxide of the same metal, enriched with Ca, P, Si, Na and at least one metal selected from the group consisting of: Ag and Ga, wherein said process consists of the following steps:
   a) cleaning the metal substrate by immersing the substrate in an ultrasound tray containing acetone for a first period of time of from 3 to 5 minutes and distilled water for a second period of time of from 3 to 5 minutes
   b) subjecting the metal substrate to an anodic spark deposition (ASD) treatment in an aqueous solution comprising sodium silicate hydrate ($Na_2SiO_3.2H_2O$), β-glycerophosphate(β-GP), calcium acetate hydrate ($C_4H_6CaO_4.2H_2O$), sodium hydroxide (NaOH), at least one compound selected from the group consisting of: elemental Ag nanoparticles, an Ag and a Ga salt
   c) cleaning the metal substrate with water by immersing the metal substrate coming from step b) in distilled water and finally drying the same.

2. The process as claimed in claim 1, wherein said Ag and Ga salt is selected from the group consisting of silver nitrate ($AgNO_3$), silver acetate ($CH_3COOAg$), and gallium nitrate $Ga(NO_3)_3$.

3. The process as claimed in claim 2, wherein when an Ag and Ga salt is in the ASD treatment, a chelating agent is also added.

4. The process as claimed in claim 3, wherein said chelating agent is selected from the group consisting of: L-cysteine ($HSCH_2CH(NH_2)CO_2H$), oxalic acid dehydrate ($HO_2CCO_2H*H_2O$).

5. The process as claimed in claim 3 wherein the deposition aqueous solution of step b) comprises the sodium silicate hydrate at the concentration of 0.005 M to 0.1 M, the β-glycerophosphate at a concentration of 0.03 M to 0.2 M, the calcium acetate hydrate at a concentration of 0.05 M to 0.6 M, and the NaOH at a concentration of 0.005 M to 0.4 M, the elemental silver nanoparticles at a concentration of from 1 to 10 g/l the silver and gallium salt at a concentration of from 0.001 to 0.01 M.

6. The process as claimed in claim 3 further containing from 0.001 to 0.5 M of the chelating agent.

7. The process as claimed in claim 5, wherein the deposition aqueous solution comprises 0.03 M sodium silicate hydrate, 0.1 M β-glycerophosphate, 0.3 M calcium acetate hydrate and 0.036M NaOH.

8. The process as claimed in claim 7 wherein said aqueous solution contains 3 g/l elemental Ag nanoparticles with a particle size between 10 and 250 nm.

9. The process as claimed in claim 7 wherein said aqueous solution contains 0.004M silver nitrate and 0.002 M L-cysteine.

10. The process as claimed in claim 7 wherein said aqueous solution contains 0.004 M gallium nitrate and 0.006 M L-cysteine.

11. The process as claimed in claim 7, wherein said aqueous solution contains 0.004M gallium nitrate and 0.306 M oxalic acid.

12. The process as claimed in claim 1, wherein the ASD treatment step is performed at a temperature comprised in an interval of 0±0.5° C.

13. The process as claimed in claim 1, wherein the ASD treatment is performed by working at a first current density value of 5 to 50 mA/cm$^2$ with a potential that increases freely up to a value of from 210 to 330 V, for a period of time needed to reach said potential value and a second current density value of 50% to 5% of said first current density.

14. The process as claimed in claim 13, wherein the ASD treatment step is performed by working at a first current density value of 10 mA/cm$^2$, with a potential that increases up to a value comprised between 300 and 325 V, for a period of time needed to reach said potential value and a second current density value of 20%, of said first current density value.

15. The process as claimed in claim 1, wherein the metal substrate is a prosthesis or a surgical implant.

* * * * *